United States Patent [19]

Asselin et al.

[11] 4,128,560

[45] Dec. 5, 1978

[54] TRICYCLIC ALKYLAMINE DERIVATIVES

[75] Inventors: Andre A. Asselin, Lemoyne; Leslie G. Humber; Thomas A. Dobson, both of Dollard des Ormeaux, all of Canada

[73] Assignee: Ayerst McKenna & Harrison Ltd., Montreal, Canada

[21] Appl. No.: 676,173

[22] Filed: Apr. 12, 1976

Related U.S. Application Data

[63] Continuation of Ser. No. 480,460, Jun. 18, 1974, abandoned.

[51] Int. Cl.$^2$ ............................................. C07D 209/86
[52] U.S. Cl. ............................... 260/315; 260/326.27; 260/326.5 B; 260/326.9; 424/274
[58] Field of Search ............ 260/315, 326.27, 326.5 B, 260/326.9

[56] References Cited

U.S. PATENT DOCUMENTS

| 3,769,298 | 10/1973 | McManus et al. | 260/315 |
| 3,859,304 | 1/1975 | Dostert et al. | 260/315 |

*Primary Examiner*—Henry R. Jiles
*Assistant Examiner*—R. W. Ramsuer
*Attorney, Agent, or Firm*—Arthur E. Wilfond

[57] ABSTRACT

Tricyclic alkylamines, and their acid addition salts with pharmaceutically acceptable acids, are disclosed. The tricyclic ring system for these compounds is selected from the group consisting of 1,2,3,4-tetrahydrocyclopent[b]indole, 1,2,3,4-tetrahydrocarbazole and 5,6,7,8,9,10-hexahydrocyclohept[b]indole. The compounds are characterized further in that the ring system carbon atom bearing the alkylamine residue is carbon atom 3, 1 and 6 in the respective ring systems and in each case the said carbon atom also is substituted with a lower alkyl. The tricyclic alkylamines are useful antidepressant agents. Methods for their preparation and use are disclosed.

22 Claims, No Drawings

TRICYCLIC ALKYLAMINE DERIVATIVES

This is a continuation, of application Ser. No. 480,460, filed June 18, 1974 now abandoned.

BACKGROUND OF THE INVENTION (a) Field of Invention

This invention relates to tricyclic alkylamine compounds, to their preparation and use, and to intermediates for their preparation.

More specifically, this invention relates to tricyclic alkylamine derivatives in which the tricyclic portion thereof is characterized by having an indole portion fused to a cyclopentane, cyclohexane or cycloheptane ring. Still more specifically, the compounds of this invention are characterized as derivatives of one of the following tricyclic ring systems:

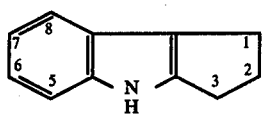

(a) 1,2,3,4-tetrahydrocyclopent[b]indole,

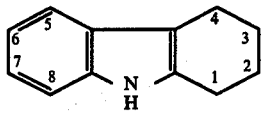

(b) 1,2,3,4-tetrahydrocarbazole, or

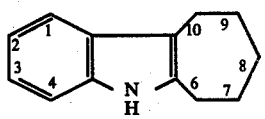

(c) 5,6,7,8,9,10-hexahydrocyclohept[b]indole, in which the carbon atom bearing the alkylamine residue is carbon atom 3, 1 and 6 in the respective ring system. In each case the carbon atom bearing the alkyl amine is substituted further with a lower alkyl.

(b) Prior Art

Apparently, the closest prior art to the compounds of the present invention is the recent German Offenlegungsschrift No. 2,263,682, published July 4, 1973, corresponding to U.S. Pat. No. 3,859,304, and which describes a series of carbazole-1-alkylamines. Although the latter compounds are claimed to be antidepressive agents, the compounds of the present invention are distinguished readily from these prior art compounds by their structural arrangement and pharmacologic properties. More particularly, they are distinguished by their increase in antidepressant potency and improved therapeutic ratio and by the fact that in the compounds of this invention the carbon atom bearing the alkylamine is fully substituted whereas in the prior art compounds the corresponding carbon atom is not.

Other prior art, although somewhat further removed, is exemplified by U.S. Pat. No. 3,592,824, issued July 13, 1971 and U.S. Pat. No. 3,634,420, issued Jan. 11, 1972. Although these examples of prior art disclose carbazolealkylamines, the fact that the disclosed compounds bear no substituent whatsoever at position 1 readily distinguishes them from the compounds of the present invention.

SUMMARY OF THE INVENTION

The compounds of this invention are represented by formula 1,

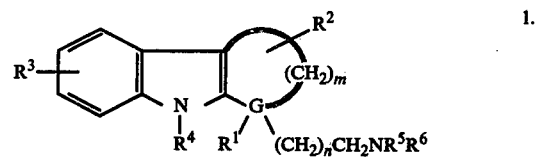

in which $R^1$ is lower alkyl, $R^2$ is hydrogen or lower alkyl, $R^3$ is hydrogen, lower alkyl, halo, hydroxy, lower alkoxy, lower alkanoyloxy or trihalomethyl, $R^4$ is hydrogen or lower alkyl, $R^5$ and $R^6$ are the same or different selected from the group of hydrogen or lower alkyl, m is an integer from two to four and n is an integer from zero to two; and the acid addition salts thereof with pharmaceutically acceptable acids.

The compounds of this invention are prepared by a process in which a hydrazine of formula 2,

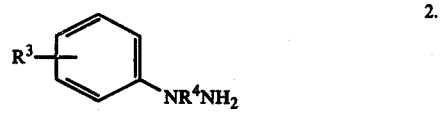

in which $R^3$ and $R^4$ are as defined herein is condensed with a compound of formula 3,

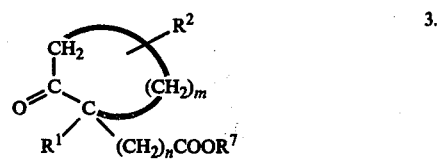

in which $R^1$, $R^2$, m and n are as defined herein and $R^7$ is hydrogen or lower alkyl to give the corresponding hydrazone of formula 4,

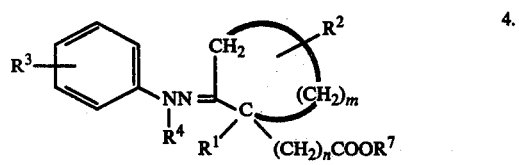

in which $R^1$, $R^2$, $R^3$, $R^4$, $R^7$, m and n are as defined herein. The hydrazone is reacted with a cyclizing agent to give the corresponding tricyclic compound of formula 5,

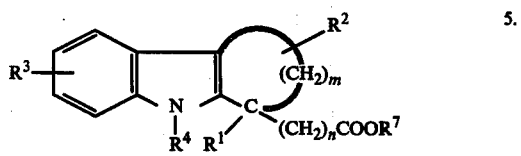

in which $R^1$, $R^2$, $R^3$, $R^4$, $R^7$, m and n are as defined herein and, in the case when the hydrazone is one of formula 4 in which $R^4$ is hydrogen, $R^7$ is lower alkyl and m and n are either the integers two and two, three and two, four and one, or four and two, respectively, also obtaining the corresponding tetracyclic compound of formula 6,

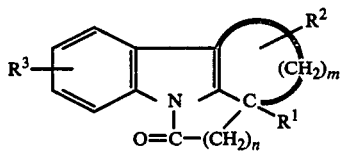

in which $R^1$, $R^2$ and $R^3$ are as defined herein and m and n are as defined in the last instance.

Thereafter, in the case of the compound of formula 5 in which $R^7$ is lower alkyl or the tetracyclic compound of formula 6, the compound is subjected to hydrolysis conditions to obtain the corresponding acid of formula 5 in which $R^7$ is hydrogen.

At this point the instant acid of formula 5 in which $R^4$ is hydrogen is subjected to optional N-alkylation with a lower alkyl halide to obtain the corresponding acid compound of formula 5 in which $R^4$ is lower alkyl.

Finally, the instant acid of formula 5 is transformed into the corresponding tricyclic alkylamine of formula 1 by (a) subjecting the acid compound of formula 5 to amidation with an appropriate amine of formula $NHR^5R^6$ in which $R^5$ and $R^6$ are as defined herein to give the corresponding amide, and reducing the amide with a suitable complex metal hydride, or (b) in the case where n is the integer one or two, subjecting the acid compound of formula 5 to the conditions of the Curtius reaction.

DETAILED DESCRIPTION OF THE INVENTION

The term "lower alkyl" as used herein contemplates straight chain alkyl radicals containing from one to six carbon atoms and branched chain alkyl radicals containing from three to four carbon atoms and includes methyl, ethyl, propyl, isopropyl, butyl, isobutyl, 2-methylpentyl, hexyl and the like.

The term "halo" as used herein contemplates halogens and includes fluorine, chlorine, bromine and iodine.

The term "lower alkoxy" as used herein contemplates both straight and branched chain alkoxy radicals containing from one to four carbon atoms and includes methoxy, ethoxy, isopropoxy, t-butoxy and the like.

The term "lower alkanoyloxy" as used herein contemplates both straight and branched chain alkanoyloxy radicals containing from two to six carbon atoms and includes acetoxy, propionyloxy, pivaloyloxy, hexanoyloxy and the like.

The term "trihalomethyl" as used herein contemplates trifluoromethyl, trichloromethyl and tribromomethyl.

The tricyclic alkylamine compounds of this invention form acid addition salts with pharmaceutically acceptable acids. Such acid addition salts are included within the scope of this invention.

The acid addition salts are prepared by reacting the base form of the appropriate tricyclic alkylamine of formula 1 with substantially one equivalent or preferably with an excess of the appropriate acid in an organic solvent, for example, ether or an ethanol-ether mixture. These salts, when administered to mammals, possess the same pharmacologic activities as the corresponding bases. For many purposes it is preferable to administer the salts rather than the base compounds. Among the acid addition salts suitable for this purpose are salts such as the sulfate, phosphate, lactate, tartrate, maleate, citrate, hydrobromide and hydrochloride. Both the base compounds and the salts have the distinct advantage of possessing a relatively low order of toxicity.

Also included in this invention are the stereochemical isomers of the compounds of formula 1 which result from asymmetric centers contained therein. These isomeric forms may be prepared by chemical methods and are purified readily by crystallization or chromatography.

Individual optical isomers, which might be separated by fractional crystallization of the diastereoisomeric salts formed thereof, for instance, with d- or l-tartaric acid or D-(+)-α-bromocamphor sulfonic acid, are also included.

ANTIDEPRESSANT ACTIVITY

The useful antidepressant activity of the tricyclic alkylamines of formula 1 and their acid addition salts with pharmaceutically acceptable acids may be demonstrated in standard pharmacologic tests; for example, the tests described by F. Hafliger and V. Burckhard in "Psychopharmacological Agents", M. Gordon, Ed., Academic Press, New York and London, 1964, pp. 75–83.

More specifically, as noted in the latter reference the antidepressant properties of a compound may be demonstrated by its capacity to antagonize the depressant effects of reserpine. Furthermore, it is well documented that reserpine in animals produces a model depression which can be used for detecting antidepressant properties. Accordingly, the compounds of the present invention antagonize reserpine effects in mice at doses ranging from about 0.5 to 100 mg/kg. Several of the preferred compounds, for instance, N,N,1,9-tetramethyl-1,2,3,4-tetrahydrocarbazole-1-ethanamine hydrochloride (Example 226), 1,2,3,4-tetrahydro-N,N,1-trimethyl-9-propylcarbazole-1-ethanamine hydrochloride (Example 226), and 1,9-diethyl-1,2,3,4-tetrahydro-N,N-dimethylcarbazole-1-ethanamine hydrobromide (Example 226), antagonize the effects of reserpine in mice at doses ranging from about 0.5 to 5.0 mg/kg.

When the tricyclic alkylamines of this invention are used to relieve the symptoms of depression in warmblooded mammals, e.g. rats and mice, they may be used alone or in combination with pharmacologically acceptable carriers, the proportion of which is determined by the solubility and chemical nature of the compound, chosen route of administration and standard biological practice. For example, they may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstance is reached. In general, the compounds of this invention are most desirably administered at a concentration level that will generally afford effective results without causing any harmful or deleterious side effects and preferably at a level that is in a range of from about 0.1 mg to about 50 mg per kilo per day, although as aforementioned variations will occur. However, a dosage level that is in the range of from about 0.1 mg to about 25 mg per kilo per day is most desirably employed in order to achieve effective results.

PROCESS

The requisite starting materials of formula 2, phenylhydrazine or substituted phenylhydrazines are known or are prepared according to known methods. A convenient method for preparing the substituted phenylhydrazines involves the diazotization of the appropriately substituted aniline to give the corresponding diazo derivative. The latter compound is then reduced with stannous chloride or sodium sulfite to give the corresponding phenylhydrazine, see L. F. Fieser and M. Fieser, "Advanced Organic Chemistry", Reinhold Publishing Corporation, New York, 1961, p. 734.

The requisite starting materials of formula 3 are either known, for example, 1-methyl-2-oxocyclohexanecarboxylic acid ethyl ester, R. Grewe, Chem. Ber., 76, 1072 (1943), 1-isopropyl-4-methyl-2-oxocyclohexanecarboxylic acid ethyl ester, A. Einhorn and Z. Klages, Chem. Ber., 34, 3793 (1901), 1-methyl-2-oxocyclohexaneacetic acid methyl ester, H. O. House and B. M. Frost, J. Org. Chem., 30, 2502 (1965), or they are prepared by several known methods. Some of the preferred methods are illustrated in the following flow diagram in which $R^1$, $R^2$, $R^7$ and m are as defined herein, $R^8$ is hydroxy or butylthio and $R^9$ is lower alkyl:

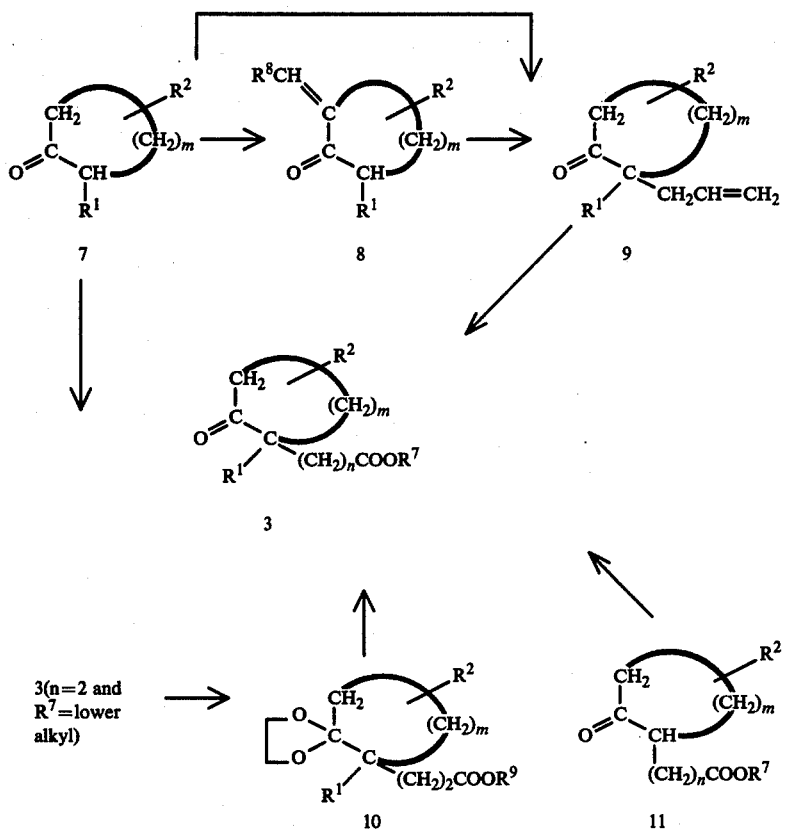

With reference to the first process for preparing the starting material, the substituted cycloalkanone of formula 7 is transformed into its corresponding hydroxymethylene derivative of formula 8 in which $R^1$, $R^2$ and m are as defined in the first instance and $R^8$ is hydroxy by treatment with ethyl formate in the presence of sodium hydride. In turn the hydroxymethylene derivative reacts readily with butanethiol to afford the corresponding butylthiomethylene derivative of formula 8 in which $R^1$, $R^2$ and m are as defined in the first instance and $R^8$ is butylthio. The latter compound is then subjected to alkylation with allyl bromide or allyl chloride in the presence of a proton acceptor, preferably sodium tert-amylate or potassium tert-butoxide, to give the corresponding butylthiomethylene derivative of the ketone of formula 9. Subsequent removal of the butylthiomethylene blocking group by heating the latter derivative in aqueous diethyleneglycol with sodium or potassium hydroxide [see R. E. Ireland and J. A. Marshall, J. Amer. Chem. Soc., 81, 6336 (1959)] yields the corresponding ketone of formula 9. The ketone of formula 9 is obtained alternatively by reacting the appropriate substituted cycloalkanone of formula 7 directly with allyl bromide or chloride in the presence of a strong proton acceptor, for example, sodium tert-amylate, potassium tert-butoxide, sodamide, sodium hydride and the like, according to the method of J. M. Conia and F. Leyendecker, Bull. Soc. Chem. Fr., 830 (1967).

Oxidation of the ketone of formula 9 with ruthenium tetroxide-sodium metaperiodate according to the method of S. C. Welch and R. Y. Wong, Tetrahedron Letters, 1853 (1972) gives the desired starting material of formula 3 in which R⁷ is hydrogen and n is the integer one. Thereafter, if desired, the latter compound, a cycloalkanoneacetic acid derivative, is converted to its corresponding lower alkyl ester derivative of formula 3 by standard esterification methods; for example, by treatment with a lower alkanol in the presence of an acid, for instance, methanol and hydrogen chloride, or by treatment with an alkyl halide in the presence of a proton acceptor, for instance, methyl iodide and potassium carbonate.

Alternatively, the latter starting material is obtained by condensing the aforementioned substituted cycloalkanone of formula 7 with an acrylic acid lower alkyl ester, preferably methyl acrylate, in the presence of potassium tert-butoxide according to the method of H. House and M. Schellenbaum, J. Org. Chem., 28, 34 (1963), to obtain the cycloalkanonepropionic acid lower alkyl ester of formula 3 in which $R^1$, $R^2$, and m are as defined hereinbefore, $R^7$ is lower alkyl and n is the integer two. The latter compound is a cycloalkanonepropionic acid lower alkyl ester, i.e. a starting material of formula 3, and when desired is converted to its corresponding acid by hydrolysis, preferably by treatment with an acid, preferably hydrochloric or sulfuric acid, in the presence of sufficient water to effect hydrolysis.

Returning now to the alternate process for preparing the cycloalkanoneacetic acid derivatives of formula 3, the aforementioned cycloalkanonepropionic acid lower alkyl ester is converted to its corresponding ethylene ketal derivative of formula 10 with ethylene glycol and an acid catalyst, preferably p-toluenesulfonic acid. Thereafter, the ketal derivative is subjected to a Barbier‐Wieland degradation according to the method of G. Stork, et al., J. Amer. Chem. Soc., 85, 3419 (1953). More specifically, the ketal 10 is first treated with an excess of phenyl magnesium bromide or chloride to give the corresponding diphenyl tertiary alcohol which on simultaneous deketalization and dehydration with aqueous acetic acid, and subsequent oxidation of the resulting keto olefin with ruthenium tetroxide-sodium metaperiodate in the same manner as described above gives the corresponding desired starting material of formula 3 in which $R^7$ is hydrogen and n is the integer one. If desired the latter compound is converted to its corresponding lower alkyl ester by esterification in the manner described previously to give the desired starting material of formula 3 in which $R^7$ is lower alkyl.

Again alternatively, a third method for preparing the starting material of formula 3 comprises the direct alkylation of the corresponding cycloalkanonealkanoic acid lower alkyl ester of formula II in which $R^2$, m and n are as defined above and $R^7$ is lower alkyl with the appropriate lower alkyl, bromide, chloride or iodide in the presence of a suitable proton acceptor, preferably sodium tert-amylate or potassium tert-butoxide, according to the method of Conia and Leyendecker, cited above, followed again by optional esterification as described above.

The substituted cycloalkanone utilized for the first two processes for preparing the starting material are either known, for example, 2-methylcyclohexanone and 2-ethylcyclohexanone or are prepared by known methods, for example, see "Rodd's Chemistry of Carbon Compounds", 2nd Ed., S. Coffey, Ed., Elsevier Publishing Company, Amsterdam, Vol. 2A, 1967, pp. 64–168 and Vol. 2B, 1968, pp. 92–113.

Likewise the cycloalkanoneacetic acid lower alkyl esters of formula 11 required for the aforementioned methods are also known, for example, 2-oxocyclohexaneacetic acid ethyl ester, or they are prepared by a known method, for example, see "Chemistry of Carbon Compounds", E. H. Rodd, Ed., Elsevier Publishing Co., Amsterdam, Vol. 2A, 1953, pp. 121 and 232–248.

Still another preparation of the compound of formula 3 in which n is the integer one is realized by subjecting an appropriately substituted 2-ketocycloalkaneacetonitrile of formula 12

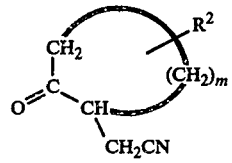

in which $R^2$ and m are as defined in the first instance to alkylation with the appropriate lower alkyl, bromide, chloride or iodide in the presence of a suitable proton acceptor, preferably sodium tert-amylate or potassium tert-butoxide, according to the method of Conia and Leyendecker, cited above, to give the corresponding compound of formula 13

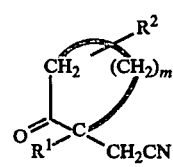

in which $R^1$, $R^2$ and m are as defined in the first instance. Thereafter the latter compound is subject to basic hydrolysis, preferably using sodium or potassium hydroxide as the base, to give the corresponding starting material of formula 3 in which n is the integer one.

The requisite 2-ketocycloalkaneacetonitriles are either known or are prepared by the method of G. Stork, et al., J. Amer. Chem. Soc., 85, 207 (1963).

The above starting materials of formula 2 and formula 3 are used to prepare the compounds of this invention in the following manner:

The starting material of formula 2 is condensed with substantially one molar equivalent of the starting material of formula 3 to give the corresponding hydrazone of formula 4 in which $R^1$ to $R^4$ inclusive, $R^7$, m and n are as defined in the first instance.

Generally speaking, the condensation is performed preferably in an inert atmosphere, for example, nitrogen or argon. Although not essential it is convenient to effect the condensation in an inert solvent. Suitable solvents include the lower alkanols such as methanol and ethanol; aromatics such as benzene and toluene; the ethers, such as tetrahydrofuran, diethyl ether, dioxane, bis(2-methoxyethyl)ether and the like; and the halogenated hydrocarbons, methylene chloride, chloroform and the like. Methanol and ethanol are especially convenient and practical solvents. Times and temperatures for the condensation generally range from 5 minutes to 2 or 3 days at 0° to 100° C. Convenient time and temperature ranges include 20° C. to the boiling point of the mixture and 15 minutes to 24 hours. Optionally this condensation is effected in the presence of an acid catalyst. In practice it has been found advantageous to employ the acid catalyst when m of the starting material of formula 3 is the integer two or four (i.e. the starting material is a cyclopentanone- or cycloheptanone-alkanoic acid or lower alkyl ester thereof). Useful acid catalysts for this purpose include p-toluenesulfonic acid, hydrogen chloride, hydrogen bromide, phosphoric acid, sulfuric acid, aluminum chloride, zinc chloride, hydrogen bromide in acetic acid, boron trifluorideetherate and trifluoroacetic acid. The amount of acid catalyst employed in this instance generally ranges from about 0.01 to 5.0 molar equivalents with respect to the hydrazine reactant, a range of 0.1 to 1.1 being preferred. Again optionally, one may employ the acid addition salts of the hydrazine reactant, for example, hydrazine hydrochloride or hydrazine sulfate, as the starting material of formula 2 for this condensation.

The resulting hydrazone 4 is cyclized to the tricyclic ester of formula 5 by the action of a suitable cyclization agent according to the conditions of the "Fischer Indole Synthesis", for example, see B. Robinson, Chem. Rev., 63, 373 (1963). A variety of cyclization agents are effective for this purpose; suitable agents include the aforementioned acid catalyst as well as cationic ion exchange resins such as Amberlite IR-120, phenyl or ethyl magnesium bromide and aniline salts. In other words the usual catalysts employed for the "Fischer Indole Synthesis" are efficacious; the preferred cyclization agents being aqueous solutions of strong acids, for example, 10 to 20% aqueous sulfuric acid, concentrated hydrochloric acid or 10% phosphoric acid.

In practice the isolation of the hydrazone 4 from the reaction mixture in which it is found is optional. Moreover, the cyclization agent may be added along with the reactants (compounds 2 and 3) to the initial reaction mixture or to the condensation mixture containing the hydrazone 4 or to the isolated hydrazone optionally dissolved in one of the above inert solvents. Under any of these conditions the hydrazone cyclizes to give the corresponding tricyclic acid or ester of formula 5 in which $R^1$ to $R^4$ inclusive, $R^7$, m and n are as defined hereinbefore.

The cyclization usually proceeds smoothly and rapidly. Convenient reaction times for the cyclization include five minutes to two hours, preferably 5 to 30 minutes and convenient temperatures include 20° and 200° C., preferably 120° to 180° C.

It should be noted that under certain circumstances a useful by-product results from the cyclization reaction. However, the formation of this by-product does not interfere with the practice of the overall process of this invention since this by-product is transformed readily to the next intermediate of the process. More specifically, when the hydrazone being cyclized is one of formula 4 in which $R^4$ is hydrogen, $R^7$ is lower alkyl and m and n, respectively, are integers selected from the group consisting of two and two, three and two, four and one, and four and two, then the corresponding tetracyclic compound of formula 6 in which $R^1$, $R^2$ and $R^3$ are as defined herein and m and n are as defined in the last instance is obtained. In other words, ester hydrazones having a hydrogen atom on one nitrogen atom and a propionic ester side chain on a cyclopentanone, cyclohexanone or cycloheptanone portion thereof, or an acetic ester side chain on a cycloheptanone portion thereof, will give rise to the corresponding tetracyclic compound of formula 6. As will be noted hereinafter this tetracyclic compound is transformed readily into the corresponding tricyclic acid of formula 5 in which $R^7$ is hydrogen under basic hydrolysis conditions.

In practice a most convenient and practical procedure for effecting the above cyclization comprises evaporating solvent from the condensation reaction mixture containing the hydrazone, and then heating the hydrazone at 120° to 200° C. in one of the aforementioned solutions of strong acids; the use of an inert solvent during the cyclization being omitted. Incidentally, by following this latter procedure the formation of an undesirable byproduct of formula 14

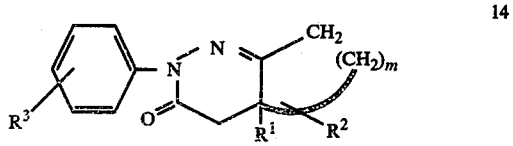

in which $R^1$, $R^2$, $R^3$ and m are as defined in the first instance, occurring when $R^4$ of the hydrazone involved represents hydrogen and n represents the integer one, is substantially reduced by the use of the higher reaction temperatures and strong acid solutions. The products of the cyclization reaction are separated and purified readily by conventional techniques. Extraction and chromatography are preferred techniques for this purpose.

As noted previously the starting material of formula 3 is either a cycloalkanonealkanoic acid derivative ($R^7$ = hydrogen) or its corresponding lower alkyl ester ($R^7$ = lower alkyl). Accordingly, when $R^7$ of the starting material is hydrogen the above process yields the tricyclic compound of formula 5 in which $R^7$ is hydrogen; and when $R^7$ of the starting material is lower alkyl the above process yields the tricyclic ester of formula 5 in which $R^7$ is lower alkyl and in the instances noted above, the corresponding tetracyclic compound of formula 6. In the latter case, the next step of the process is the conversion of the tricyclic ester or the tetracyclic compound to its corresponding tricyclic ester of formula 5 in which $R^7$ is hydrogen. This conversion is effected most conveniently by subjecting the tricyclic ester, or the tetracyclic compound to the action of a base in the presence of sufficient water to effect hydrolysis. A preferred embodiment involves subjecting the compound to the action of sodium or potassium carbonate in aqueous methanol or ethanol. The reaction mixture is maintained at a temperature of from 25° C. to the reflux temperature until hydrolysis occurs. Usually from 10 minutes to 48 hours is sufficient for this hydrolysis. The reaction mixture is then rendered acidic with an acid, for example, acetic acid, hydrochloric acid, sulfuric acid and the like, to release the free acid.

Generally, this conversion is most conveniently performed by employing a base as the hydrolyzing agent. However, the manner of hydrolysis is not intended to be limited to basic hydrolysis since hydrolysis under acidic conditions and other variations, for example, treatment with lithium iodide in collidine (see L. F. Fieser and M. Fieser, "Reagents for Organic Synthesis", John Wiley and Sons, Inc., New York, 1967, pp. 615–617) are also applicable.

In the manner set out and described above, the process of this invention at this point affords the tricyclic acid of formula 5 in which $R^7$ is hydrogen.

A convenient option regarding the ultimate preparation of the compounds of formula 1 in which $R^4$ is lower alkyl can be effected at this point. We have found that the tricyclic acids of formula 5 in which $R^4$ is hydrogen are alkylated most conveniently and efficaciously on the indolic nitrogen atom. Accordingly, N-alkylation at this point of the process represents an attractive alternative for the preparation of the N-alkylated tricyclic acids of formula 5 in which $R^4$ is lower alkyl and $R^7$ is hydrogen. The N-alkylation is carried out preferably by reacting the tricyclic acid of formula 5 ($R^4$ and $R^7$ = hydrogen) with the appropriate lower alkyl halide in the presence of one of the aforementioned suitable proton acceptors, preferably sodium hydride. Suitable solvents for this N-alkylation include tetrahydrofuran, dioxane, dimethylformamide and dimethylsulfoxide; tetrahydrofuran being preferred. Convenient reaction times and temperatures include one to 24 hours at 20° to 80° C.

The instant tricyclic acids of formula 5 are converted to the tricyclic alkylamine compounds of this invention by either of the two following procedures.

In the first procedure the acid is subjected to amidation followed by reduction of the resulting amide. In a preferred embodiment the acid is subjected to amidation by treatment with a lower alkyl chloroformate, preferably ethyl chloroformate, in the presence of triethylamine, affording the corresponding mixed anhydride, which is converted by treatment with the appropriate amine of formula $HNR^4R^5$ in which $R^4$ and $R^5$ are as defined in the first instance, for example, ammonia, methylamine or dimethylamine, to yield the corresponding amide of formula 15

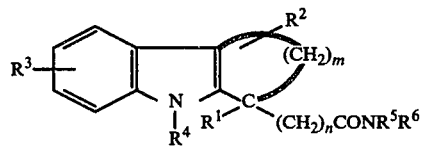

15 in which $R^1$ to $R^6$ inclusive and m and n are as defined herein.

Thereafter, the amides so obtained are reduced with a suitable complex metal hydride to yield the desired tricyclic alkylamines. Examples of suitable complex metal hydrides are lithium aluminum hydride, lithium aluminum hydride-aluminum chloride, aluminum hydride-aluminum chloride, diborane and sodium borohydride-aluminum chloride. Lithium aluminum hydride is preferred.

In the second procedure the acid is converted to a corresponding tricyclic alkylamine by a process involving the Curtius reaction. The Curtius reaction is a known method for converting an acid through its azide to an amine. The key steps are the decomposition of the acid azide to its corresponding isocyanate (Curtius rearrangement) and subsequent transformation of the isocyanate to the amine by hydrolysis or reduction. Brief reviews of this reaction have appeared in Chemical Reviews, 43, 205 (1948), by J. H. Saunders and R. J. Slocombe and in Organic Reactions 3, 337 (1946) by P. A. S. Smith.

In a preferred embodiment of this procedure, the instant acid of formula 5 in which n is the integer one or two is reacted with a lower alkyl formate, preferably methyl or ethyl chloroformate in the presence of a tertiary organic base, preferably triethylamine, to afford the corresponding mixed anhydride. The anhydride is treated with sodium or potassium azide to obtain the corresponding acid azide derivative of formula 16. Heating the latter compounds, usually at 60° to 120° C. for 15 minutes to about 6 hours, in an inert organic solvent, preferably benzene or toluene, rearranges said latter compound to the corresponding isocyanate of formula 17 in which n is zero or one, respectively.

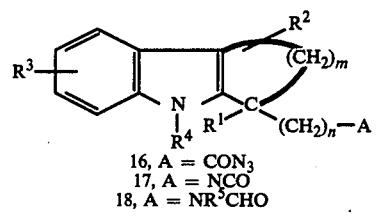

16, A = $CON_3$
17, A = NCO
18, A = $NR^5CHO$

The isocyanate is converted subsequently to the tricyclic alkylamines by employing hydrolysis or reduction and optional N-alkylation reactions.

More specifically, the tricyclic alkylamines of formula 1 in which $R^5$ and $R^6$ are both hydrogen are obtained by hydrolysis of the isocyanate. Such hydrolysis is effected readily by heating the isocyanate with 10 to 20% hydrochloric acid for about 8 to 24 hours.

If desired the latter compounds of formula 1, a primary amine, is further N-alkylated on the nitrogen of the primary amine with an appropriate lower alkyl halide to give the corresponding compounds of formula 1 in which $R^5$ is hydrogen or lower alkyl and $R^6$ is lower alkyl (i.e. secondary or tertiary amines with respect to the nitrogen atom in the side chain).

Depending on the particular derivative desired, the N-alkylation is effected with one or two moles of the alkyl halide to give respectively the secondary ($R^5$ = H and $R^6$ = lower alkyl) or tertiary amine ($R^5$ = $R^6$ = lower alkyl). On the other hand the N-alkylation may be done in two steps by introducing a different alkyl group each time to afford the corresponding tertiary amine in which $R^5$ and $R^6$ are different lower alkyls. It should be kept in mind that if the compound being alkylated under these present conditions is unsubstituted on the indolic nitrogen, N-alkylation of the indolic nitrogen will occur also.

When it is desired to prepare the above tertiary amine compounds in which either $R^5$ or $R^6$ is methyl or both are methyl an alternative alkylation method especially useful for preparing tertiary amine compounds of formula 1 in which n is the integer two comprises reacting the appropriate corresponding primary or secondary amine with an aqueous mixture of a substantial excess of formaldehyde and formic acid according to the conditions of the Eschweiler-Clarke reaction, see M. L. Moore, Organic Reactions, 5, 301 (1949), whereby N-methylation is effected.

Another N-alkylation method which may be applied to the above primary and secondary amines involves acylation with a lower alkanoic anhydride or acid halide and subsequent reduction of the resulting amide.

Still more specifically the tricyclic alkylamines of formula 1 in which $R^5$ is hydrogen or methyl and $R^6$ is methyl are prepared by the following convenient process:

The aforementioned isocyanate of formula 17 is reduced to the corresponding formamide of formula 18 in which n is the integer one or two and $R^5$ is hydrogen. This reduction is effected by using either formic acid, sodium borohydride or triphenyltin hydride as the reducing agent. Thereafter, the formamide is either reduced with one of the aforementioned suitable complex metal hydrides, preferably lithium aluminum hydride, to give the corresponding tricyclic alkyl (secondary) amine of formula 1 in which $R^5$ is hydrogen and $R^6$ is methyl, or the formamide is N-alkylated with a methyl halide, as described hereinbefore, and reduced with a complex metal hydride, as described hereinbefore, to give the corresponding tricyclic alkyl (tertiary) amine of formula 1 in which $R^5$ and $R^6$ are both methyl. Alternatively, said N-alkylated formamide is subjected to basic hydrolysis conditions to give the corresponding tricyclic alkyl (secondary) amine.

The following examples illustrate further this invention.

EXAMPLE 1

2-isopropylphenylhydrazine (2, $R^3$ = 2-CH(CH$_3$)$_2$ and $R^4$ = H)

A mixture of the substituted aniline, 2-isopropylaniline (27g, 0.2 mole), concentrated hydrochloric acid (150 ml) and water (160 ml) is stirred mechanically for 30 minutes at room temperature. After cooling to 0° C., the mixture is diazotized by adding dropwise a solution of sodium nitrite (14 g, 0.203 mole) in water (140 ml) over a period of 20 minutes. Stirring is continued for an additional one hour at 0° C. The diazo solution is reduced by adding dropwise a solution of stannous chloride dihydrate (112 g, 0.497 mole) in concentrated hydrochloric acid (90 ml) over a period of 30 minutes at −10° C. to −15° C. The reaction mixture is stirred for an additional 1.5 hour at −10° C. to −15° C. The precipitate is collected by filtration to give the hydrochloric acid addition salt of the title compound. The salt is purified further by dissolving it in ethanol, concentrating the solution and adding a saturated solution of hydrochloric acid in ether to give the hydrochloride salt with mp 206°-210° C.

By following the procedure of this example and using the appropriate substituted aniline then other substituted hydrazines of formula 2, for example those described as starting materials in Examples 12–55, are obtained. More specifically exemplified, the replacement of 2-isopropylaniline with an equivalent amount of 2-propylaniline gives 2-propylphenylhydrazine hydrochloride, mp 182°-184° C. Similarily, replacement with 2-ethylaniline gives 2-ethylphenylhydrazine hydrochloride, mp 181°-183° C.

EXAMPLE 2

2-Ethyl-6-(hydroxymethylene)cyclohexanone(8, $R^1$ = C$_2$H$_5$, $R^2$ = H, $R^8$ = OH and m = 3)

To a stirred suspension of sodium hydride (18.2 g of 53% oil dispersion, 0.4 mole) in dry ether cooled to 5° under nitrogen, absolute ethanol (2 ml) is added dropwise to initiate the reaction. A solution of the substituted cycloalkanone, 2-ethylcyclohexanone (50.48 g, 0.4 mole), and ethyl formate (48.0 g, 0.6 mole) is then added dropwise over a period of one hr. The mixture is stirred overnight at room temperature. To the stirred yellow suspension absolute ethanol (8 ml) in dry ether (80 ml) is added dropwise. Stirring is continued for one hr, then water (80 ml) is added. The mixture is transferred to a separatory funnel, shaken well and the organic layer separated. The organic layer is washed once with water. The aqueous layers are combined, washed once with ether and rendered acidic by the careful addition of 6N HCl.

The acidic solution is extracted with ether (3 ×). The ether extracts are washed once with brine, dried (MgSO$_4$) and concentrated. The residue (57.2 g) is distilled to give the title compound, bp 82°-84° C./8mm, nmr (CDCl$_3$) δ 8.65 (s, 1H), 14.70 (broad s, 1H).

EXAMPLE 3

2-[(Butylthio)methylene]-6-ethylcyclohexanone (8, $R^1$ = C$_2$H$_5$, $R^2$ = H, $R^8$ = n-C$_4$H$_9$S and m = 3)

A solution of 2-ethyl-6-(hydroxymethylene)cyclohexanone (43.0 g, 0.277 mole), described in Example 2, butylmercaptan (28.6 g, 0.318 mole) and p-toluenesulfonic acid (50 mg) in dry benzene (200 ml) is heated at reflux under nitrogen for 4 hr using a Dean-Stark water separator. The reaction mixture is cooled and washed with saturated aqueous sodium bicarbonate (50 ml), water and brine, then dried (MgSO$_4$). After removal of the solvent at reduced pressure the residue is distilled to give the title compound, bp 110°-115° C./1.5 mm, nmr (CDCl$_3$) δ 0.92 (6H), 7.5 (m, 1H).

EXAMPLE 4

2-Allyl-2-ethylcyclohexanone (9, $R^1$ - C$_2$H$_5$, $R^2$ = H and m = 3)

Procedure A:

To a well stirred solution of potassium tert-butoxide (17.95 g, 0.16 mole) in dry redistilled tert-butanol (160 ml) under nitrogen, 2-[(butylthio)methylene]6-ethylcylcohexanone (9.05 g, 0.04 mole), described in Example 3, is added slowly. The mixture is stirred at room temperature for 5 minutes and then chilled in an ice bath. Allyl bromide (21.8 g, 0.18 mole) is added rapidly to the chilled mixture. The mixture is then stirred at room temperature for 48 hr. Most of the solvent is then removed under reduced pressure and water (about 150 ml) is added. The aqueous solution is extracted with ether (3 ×). The combined ether extracts are washed with brine, dried (MgSO$_4$) and concentrated to yield an oil. The oil is subjected to chromatography on silica gel (320 g) using 4% ether in hexane as eluant. Concentration of the eluate gives 2-allyl-6-[(butylthio)methylene]-2-ethylcyclohexanone, nmr(CDCl$_3$) δ 0.85 (t, J=7, 3H), 2.85 (t, J=7, 2H), 4.80 − 6.0 (m, 3H), 7.5 (t, J=2, 1H).

A solution of the latter compound (5.23 g, 0.0196 mole) in 25% NaOH (15 ml) and diethylene glycol (15 ml) is heated at reflux overnight under nitrogen. The camphor smelling mixture is steam distilled and about 250 ml of distillate is collected. The distillate is saturated with NaCl and extracted with ether (4 × 60 ml). The combined ether extracts are washed with 25% aqueous KOH (2 × 10 ml), then brine (2 × 40 ml) and dried (MgSO$_4$). Concentration of the extract affords the title compound as an oil, nmr (CDCl$_3$) δ 0.78 (t, J=7, 3H), 2.15-2.4 (m, 4H), 4.8-6.1 (m, 3H).

Procedure B:

To a suspension of sodium hydride (55% oil dispersion, 1.74 g, 0.04 mole) in dry dimethoxyethane (75 ml) cooled to 5° C., 2-ethylcyclohexanone (5.04 g, 0.04 mole) is added dropwise over a period of 10 minutes. The reaction mixture is allowed to reach room temperature and then heated to 80° C. for ½ hr. The mixture is cooled again at 5° C. and allyl bromide (3.45 ml, 4.48g, 0.04 mole) is added dropwise. The mixture is stirred at room temperature for 1½ hr. Water (10 ml) is added dropwise and the mixture transferred to a separatory funnel. It is extracted with ether twice. The ether extracts are dried (MgSO$_4$) and concentrated to give a yellow oil. The oil is subjected to chromatography on silica gel (150 g) using 3% ether in pentane as eluant. The second main product to be eluted is the desired title compound identical to the product obtained by Procedure A.

EXAMPLE 5

1-Ethyl-2-oxocyclohexaneacetic Acid (3, $R^1 = C_2H_5$, $R^2$ and $R^7 = H$, m = 3 and n = 1)

A solution of 2-allyl-2-ethylcyclohexanone (61 g, 0.37 mole), described in Example 4, in acetone is added dropwise under nitrogen to a solution of ruthenium tetroxide (yellow) in carbon tetrachloride prepared as follows:

To ruthenium dioxide (4.7 g) in carbon tetrachloride (600 ml) stirred and cooled (ice bath) under nitrogen, sodium metaperiodate (35 g) in water (250 ml) is added rapidly. The yellow carbon tetrachloride layer is separated and used as such.

As the addition proceeds, the reaction mixture turns brown, then black as ruthenium dioxide precipitates. Reoxidation to yellow tetroxide is achieved by intermittent addition of sodium metaperiodate in aqueous solution or as a solid. Total weight of $NaIO_4$ used up: 375 g in about 2 liters of water. Some acetone is added to keep the mixture homogeneous. The temperature rises to 45° C. and some cooling is necessary to keep it around 30° C.

The reaction is over after about 4.5 hours. Some isopropanol (50 ml) is added to destroy excess tetroxide. The mixture is filtered through a layer of diatomaceous earth (Celite). The filter cake is thoroughly washed with acetone. The organic layer of the filtrate ($CCl_4$) is concentrated under reduced pressure; the aqueous layer is saturated with sodium chloride and extracted with ether (4×). The combined organic fractions are washed with saturated aqueous sodium bicarbonate (7×). The basic solution is rendered acidic by the careful addition of conc. HCl, saturated with sodium chloride and then extracted with ether (4×). The ether extracts are washed once with brine, dried ($MgSO_4$) and concentrated to afford the title compound, $\nu_{max}^{CHCl_3}$ 3400, 1770, 1715 $cm^{-1}$, m.p. 57°–63° C.

EXAMPLE 6

1-Methyl-2-oxocyclohexanepropionic Acid Methyl Ester (3, $R^1$ and $R^7 = CH_3$, $R^2 = H$, m = 3 and n = 2)

The substituted cycloalkanone, 2-methylcyclohexanone(160 g. 1.27 mole), is added dropwise to a stirred solution of potassium tert-butoxide (7.0 g, 0.062 mole) in redistilled tert-butanol (325 ml) under nitrogen, followed by the addition of methyl acrylate (102.4 g, 1.20 mole). The temperature is kept below 30° C. by intermittent use of a cooling bath. Thereafter the mixture is stirred at room temperature for 2 hr. Dilute sulfuric acid (200 ml) is then added slowly. The aqueous phase is extracted with ether. The combined organic phases are washed twice with brine, dried ($MgSO_4$) and concentrated to give a crude residue. The residue is fractionated by distillation through a 6 in. Vigreux column. The title compound distills at 106°–108°/0.4 mm, nmr ($CDCl_3$) δ 1.08 (s, 3H), 1.5–2.6 (m, 12 H), 3.66 (s, 3H).

In the same manner but replacing 2-methylcyclohexanone with an equivalent amount of 2-ethylcyclohexanone or 2-propylcyclohexanone, 1-ethyl-2-oxocyclohexanepropionic acid methyl ester, bp 117°–120° C./0.4mm, and 1-propyl-2-oxocyclohexanepropionic methyl ester, $\nu_{max}^{CHCl_3}$ 1735, 1700 $cm^{-1}$, are obtained, respectively.

In the same manner but replacing 2-methylcyclohexanone with an equivalent amount of 2-methylcyclopentanone, 1-methyl-2-oxocyclopentanepropionic acid methyl ester, bp 88°–100° C./1.1 mm, nmr ($CDCl_3$) δ 1.0 (s, 3H), 1.8 (m, 6H), 2.3 (m, 4H), 3.7 (s, 3H), is obtained.

EXAMPLE 7

6-Methyl-1,4-dioxaspiro[4.5]decane-6-propionic acid methyl ester (10, $R^1$ and $R^9 = CH_3$, $R^2 = H$ and m = 3)

A solution of 1-methyl-2-oxocyclohexanepropionic acid methyl ester (96.1 g, 0.48 mole), described in Example 6, ethylene glycol (100 ml) and p-toluenesulfonic acid (2.0 g) in dry benzene (1600 ml) is heated at reflux for 6 hr using a water separator. The benzene solution is cooled, washed with saturated aqueous sodium bicarbonate solution (2 × 100 ml) then brine (2 × 100 ml), dried ($MgSO_4$) and concentrated to yield the title compound as an oil, $\nu_{max}^{CHCl_3}$ 1725, 1085 $cm^{-1}$.

In the same manner but replacing 1-methyl-2-oxocyclohexanepropionic acid methyl ester with an equivalent amount of 1-ethyl-2-oxocyclohexanepropionic acid methyl ester or 1-propyl-2-oxocyclohexanepropionic acid methyl ester, described in Example 6, 6-ethyl-1,4-dioxaspiro[4.5]decane-6-propionic acid methyl ester, $\nu_{max}^{CHCl_3}$ 1730 $cm^{-1}$ and 6-propyl-1,4-dioxaspiro[4.5]-decane-6-propionic acid methyl ester, $\nu_{max}^{CHCl_3}$ 1735 $cm^{-1}$, are obtained, respectively.

EXAMPLE 8

1-Methyl-2-oxocyclohexaneacetic Acid (3, $R^1 = CH_3$, $R^2$ and $R^7 = H$, m = 3 and n = 1)

A solution of 6-methyl-1,4-dioxaspiro[4.5]decane-6-propionic acid methyl ester (52.5 g, 0.21 mole), described in Example 7, in anhydrous ether (500 ml) and dry benzene (100 ml) is added dropwise under nitrogen to a cooled (0°–5° C.) stirred solution of phenyl magnesium bromide in ether prepared from magnesium turnings (15.9 g, 0.65 mole), bromobenzene (75 ml, 0.72 mole) and anhydrous ether (500 ml). (Note: Only about 75 ml of ether is used to start the reaction with 15 drops methyl iodide and 2–3 ml bromobenzene). The mixture is stirred overnight at room temperature. Following the careful addition of saturated ammonium chloride solution (114 ml) with cooling, the resulting yellow ether layer is decanted and the precipitated magnesium salts are rinsed thoroughly with ether. The combined ether layers are steam distilled and methanol (100 ml) and 25% aqueous sodium hydroxide (150 ml) is added to the residue. The mixture is heated at reflux for 2 hr to saponify any unreacted ester. The methanol is evaporated and the residue is extracted with ether (4×). The ether extracts are dried ($MgSO_4$) and concentrated to give 6-methyl-α,α-diphenyl-1,4-dioxaspiro[4.5]decane-6-propanol, mp 115°–117° C. after recrystallization from chloroformhexane, $\nu_{max}^{CHCl_3}$ 3620, 3500, 1092 $cm^{-1}$.

The latter compound (35.4 g, 0.07 mole) in acetic acid (500 ml) and water (10 ml) is heated at reflux for 4 hr. Evaporation of the solvents under reduced pressure and repeated evaporation with benzene gives 2-methyl-2(3,3-diphenylallyl)cyclohexanone as an oil, $\nu_{max}^{CHCl_3}$ 1740 $cm^{-1}$.

The latter compound (2.40 g, 7.5 mmole) in acetone is oxidized with ruthenium tetroxide-sodium metaperiodate according to the procedure described in Example 5 to give the title compound, mp 87°–90° C. after recrystallization from acetone hexane.

In the same manner but replacing 6-methyl-1,4-dioxaspiro[4.5]decane-6-propionic acid methyl ester with an equivalent amount of 6-ethyl-1,4-dioxaspiro[4.5]decane-6-propionic acid methyl ester, described in Example 7, 1-ethyl-2-oxocyclohexaneacetic acid, identical to the product of the same name in Example 5, is obtained via the respective intermediates, 6-ethyl-α,α-diphenyl-1,4dioxaspiro[4.5]decane-6-propanol, $\nu_{max}^{CHCl_3}$ 3450 cm, nmr (CDCl$_3$) δ 0.75 (t, J = 7, 3H), 3.85 (s, 4H), 7.2–7.6 (m, 10H) and 2-ethyl-2-(3,3-diphenylallyl)cyclohexanone, $\nu_{max}^{CHCl_3}$ 1740 cm$^{-1}$.

Again in the same manner but replacing 6-methyl-1,4-dioxaspiro[4.5]decane-6-propionic acid methyl ester with an equivalent amount of 6-propyl-1,4-dioxaspiro[4.5]decane6-propionic acid methyl ester, described in Example 7, 2-oxo-1-propylcyclohexaneacetic acid, $\nu_{max}^{CHCl_3}$ 1775, 1710 cm$^{-1}$, is obtained via the respective intermediates, α,α-diphenyl-6-propyl-1,6-dioxaspiro[4.5]decane-6-propanol, $\nu_{max}^{CHCl_3}$ 3620, 3480, 1175, 1130, 1110, 1062 cm$^{-1}$, and 2-(3,3-diphenylallyl)-2-propylcyclohexanone, nmr (CDCl$_3$) δ 0.85 (m, 3H), 6.0 (t, 1H), 7.3 (m, 10H).

EXAMPLE 9

1-Ethyl-2-oxocyclohexaneacetic Acid Methyl Ester (3, $R^1 = C_2H_5$, $R^2 = H$, $R^7 = CH_3$, m = 3 and n = 1)

To a stirred solution (THF, 30ml) of freshly prepared 1-ethyl-2-oxocyclohexaneacetic acid (680 mg, 3.7 mmoles), described in Examples 5 and 8, under nitrogen at room temperature, anhydrous K$_2$CO$_3$ (773 mg, 5.6 mmoles) and methyl iodide (3.5 ml, 7.98 g, 56 mmoles) are added. The mixture is heated at reflux for 4.5 hr during which time an additional 3 ml of methyl iodide is added every 1.5 hr. Thereafter the solvent is removed at reduced pressure, the residue is partitioned between ether and cold water. The organic layer is separated, washed with cold water until neutral, then once with brine and dried (MgSO$_4$). Removal of the solvent at reduced pressure affords the title compound, $\nu_{max}^{CHCl_3}$ 1735, 1705 cm$^{-1}$, nmr (CDCl$_3$) δ 0.8 (t, J=7, 3H), 3.62 (s, 3H).

In the same manner but replacing methyl iodide with an equivalent amount of ethyl iodide or propyl iodide, 1-ethyl-2-oxocyclohexanceacetic acid ethyl ester and 1-ethyl-2-oxocyclohexaneacetic acid propyl ester are obtained, respectively.

In the same manner but replacing 1-ethyl-2-oxocyclohexaneacetic acid with an equivalent amount of 1-methyl-2-oxocyclohexaneacetic acid, described in Example 8, 1-methyl-2-oxocyclohexaneacetic acid methyl ester, $\nu_{max}^{CHCl_3}$ 1735, 1705 cm, nmr (CDCl$_3$) δ 1.23 (s,3H), 1.8 (m,6H), 2.1 (s, 2H), 2.6 (m,2H), 3.65 (s,3H), is obtained.

In the same manner but replacing 1-ethyl-2-oxocyclohexaneacetic acid with an equivalent amount of 2-oxo-1-propylcyclohexaneacetic acid, described in Example 8, and replacing methyl iodide with an equivalent amount of ethyl iodide, 2-oxo-1-propylcyclohexaneacetic acid ethyl ester, $\nu_{max}^{CHCl_3}$ 1725, 1705 cm, nmr (CDCl$_3$) δ 0.90 (m,3H), 1.25 (t, J = 7, 3H), 2.52 (d, J = 4, 2H), 4.15 (q, J = 7, 2H), is obtained.

By following serially the procedures of Examples 2,3,4,5 and optionally the procedure of Example 9 and using the appropriate substituted cycloalkanone then other starting materials of formula 3, for example those described as starting materials in Examples 12–55, are obtained.

EXAMPLE 10

1-Methyl-2-oxocycloheptaneacetic Acid (3, $R^1 = CH_3$, $R^2$ and $R^7 = H$, m = 4 and n = 1) and its Corresponding Methyl Ester To a stirred solution of 2-oxocycloheptaneacetonitrile (44.6 g, 0.297 mole), and methyl iodide (42.6 g, 0.3 mole) in dry benzene (200 ml) under nitrogen, is added dropwise a solution of sodium tert-amylate in toluene (340 ml, 0.297 mole). The reaction is exothermic and a bright yellow colour appears. The mixture is stirred at 65° C. for 4 hr., then allowed to stand overnight at room temperature. The mixture is washed with 1% aqueous HCl, cold water, then brine, dried (MgSO$_4$) and concentrated to give an oily residue. Distillation under reduced pressure gives 1-methyl-2-oxocycloheptaneacetonitrile (13, $R^1 = CH_3$, $R^2 = H$ and m = 4), bp 152°–158° C./14 mm.

A solution of the latter compound (34.3 g, 0.208 mole) in 10% aqueous sodium hydroxide (500 ml) is heated at reflux for 3 hr. The solution is cooled, washed twice with ether to remove any neutral compound, acidified with 6 N HCl (with cooling) saturated with sodium chloride and extracted with ether (3x). An emulsion is obtained. Upon filtration through a pad of diatomaceous earth, the ether phase is separated, washed once with brine, dried (MgSO$_4$) and concentrated to give 1-methyl-2-oxocycloheptaneacetic acid, $\nu_{max}^{CHCl_3}$ 2900, 1705 cm$^{-1}$.

Treatment of the latter compound with methyl iodide and potassium carbonate according to the procedure of Example 9 affords 1-methyl-2-oxocycloheptaneacetic acid methyl ester, $\nu_{max}^{CHCl_3}$ 1730, 1700 cm$^{-1}$.

EXAMPLE 11

1,2,3,4-Tetrahydro-1-methylcarbazole-1-acetic Acid Methyl Ester (5, $R^1$ and $R^7 = CH_3$, $R^2$, $R^3$ and $R^4 = H$, m = 3 and n = 1)

A solution of the starting material of formula 3, 1-methyl-2-oxocyclohexaneacetic acid methyl ester (18.0 g, 0.097 mole), described in Example 9, and phenylhydrazine (10.6 g, 0.097 mole) in anhydrous ethanol (300 ml) is heated at reflux under nitrogen for 4 hr. Concentration of the reaction mixture affords the corresponding phenylhydrazone of the starting material of formula 3 as a solid, mp 84.5°–86.5° C.

The phenylhydrazone is heated at reflux (bath temp = 150° C.) with an excess of 10% aqueous sulfuric acid for 15 minutes. The solution is cooled rapidly, saturated with sodium chloride and extracted with ether (4x). The ether extracts are combined and washed with 5% aqueous NaOH, dried (MgSO$_4$) and concentrated. The residue is subjected to chromatography on silica gel using 2.5% acetone in benzene as eluant. Concentration of the eluate gives the title compound, nmr (CDCl$_3$) δ 1.45 (s, 3H), 1.75–2.0 (m, 4H), 2.65 (s, 2H), 2.75 (m, 2H), 3.68 (s, 3H), 6.9–7.6 (m, 4H), 9.2 (s, 1H).

Further elution with the same eluent afforded a small amount of the by-product, 4a-methyl-2-phenyl-4,4a,5,6,7,8-hexahydro-3(2H)-cinnolinone, (14, $R^1 = CH_3$, $R^2$ and $R^3 = H$ and m = 3), mp 82°–83° C. after recrystallization from hexane.

The procedure of Example 11 is followed to prepare other compounds of formula 5 in which $R^1$, $R^2$, $R^3$, $R^4$, $R^7$, m and n are as defined in the first instance. For example, by using an equivalent amount of 1-ethyl-2-oxocyclohexaneacetic acid methyl ester, described in Example 9, instead of 1-methyl-2-oxocyclohexaneacetic acid in the procedure of Example 10, 1-ethyl-1,2,3,4-tetrahydrocarbazole-1-acetic acid methyl ester, (5, $R^1$ = $C_2H_5$, $R^2$, $R^3$ and $R^4$ = H, $R^7$ = $CH_3$, m = 3 and n = 1), mp 67°–71° C. after crystallization from benzene, is obtained via the intermediate hydrazone, 1-ethyl-2-oxocyclohexaneacetic acid methyl ester phenylhydrazone (4, $R^1$ = $C_2H_5$, $R^2$, $R^3$ and $R^4$ = H, $R^7$ = $CH_3$, m = 3 and n = 1), mp 98°–99.5° C. after recrystallization from ethanol.

Further examples of such compounds of formula 5 which can be prepared by the procedure of Example 11 are listed in Tables I, II and III. In each of these examples an equivalent amount of the hydrazine of formula 2 and the starting material of formula 3, listed therein, is used in place of the phenylhydrazine and the starting material of formula 3 noted in Example 11.

TABLE 1

| Ex. | Hydrazine of Formula 2 | | Starting Material of Formula 3 | | | | | Product: (Prefix listed below)-1,2,3,4-tetrahydrocarbazole-(suffix listed below) PREFIX//SUFFIX |
|---|---|---|---|---|---|---|---|---|
| | $R^3$ | $R^4$ | $R^1$ | $R^2$ | $R^7$ | m | n | |
| 12 | H | H | n-$C_3H_7$ | H | $C_2H_5$ | 3 | 1 | 1-propyl//1-acetic acid ethyl ester, mp 64–66° C, $\nu_{max}^{CHCl_3}$ 3400, 1715 cm$^{-1}$ |
| 12a | H | H | n-$C_3H_7$ | H | $CH_3$ | 3 | 1 | 1-propyl//1-acetic acid methyl ester, mp 88–90° C |
| 12b | H | H | n-$C_3H_7$ | H | H | 3 | 1 | 1-propyl//1-acetic acid, $\nu_{max}^{CHCl_3}$ 3490, 3430, 1705 cm$^{-1}$ |
| 13 | 2-$CH_3$ | H | $CH_3$ | H | $CH_3$ | 3 | 1 | 1,8-dimethyl//1-acetic acid methyl ester |
| 14 | 3-$C_2H_5$ | $CH_3$ | $CH_3$ | H | $CH_3$ | 3 | 1 | 5-(and 7-)ethyl-1,9-dimethyl//1-acetic acid methyl ester |
| 15 | H | $C_2H_5$ | $CH_3$ | H | H | 3 | 1 | 9-ethyl-1-methyl//1-acetic acid nmr (CDCl$_3$) δ 1.35 (t, J = 7, 3H) 1.4 (s, 3H), 4.3 (q. 2H) |
| 16 | 2-$C_2H_5$ | H | $C_2H_5$ | H | $CH_3$ | 3 | 1 | 1,8-diethyl//1-acetic acid methyl ester, mp 91–93° C |
| 17 | 2-(n-$C_3H_7$) | H | $C_2H_5$ | H | $CH_3$ | 3 | 1 | 1-ethyl-8-propyl//1-acetic acid methyl ester, mp 99–100° C |
| 18 | 2-(i-$C_3H_7$) | H | $C_2H_5$ | H | $CH_3$ | 3 | 1 | 1-ethyl-8-isopropyl//1-acetic acid methyl ester, nmr (CDCl$_3$) δ 0.85 (t, J = 7, 3H), 1.41 (d, J = 7, 6H) 1.8 (m,6), 2.7 (m,4), 3.25 (m,1H), 3.70 (s.3H), 7.2 (m,3H), 9.6 (b,1H) |
| 19 | 2-Cl | H | $C_2H_5$ | H | $CH_3$ | 3 | 1 | 8-chloro-1-ethyl//1-acetic acid methyl ester |
| 20 | 4-F | n-$C_3H_7$ | $C_2H_5$ | 4-$CH_3$ | H | 3 | 1 | 1-ethyl-6-fluoro-4-methyl-9-propyl//1-acetic acid |
| 21 | 4-$OCH_3$ | H | $C_2H_5$ | H | $CH_3$ | 3 | 1 | 1-ethyl-6-methoxy//1-acetic acid methyl ester, mp 75–78° C |
| 22 | 3-$OC_2H_5$ | H | $C_2H_5$ | 5-$C_2H_5$ | $C_2H_5$ | 3 | 0 | 1,3-diethyl-5-(and 7-)ethoxy//1-carboxylic acid ethyl ester |
| 23 | H | H | $CH_3$ | H | $CH_3$ | 3 | 0 | 1-ethyl//1-carboxylic acid methyl ester |
| 24 | 4-$OCOC_2H_5$ | H | $C_2H_5$ | H | $CH_3$ | 3 | 0 | 1-ethyl-6-propionoxy//1-carboxylic acid methyl ester |
| 25 | 2-$CF_3$ | $C_2H_5$ | $C_2H_5$ | H | $C_2H_5$ | 3 | 0 | 1,9-diethyl-8-trifluoromethyl//1-carboxylic acid ethyl ester |

TABLE 11

| Ex. | Hydrazine of Formula 2 | | Starting Material of Formula 3 | | | | | Product: (Prefix listed below)-1,2,3,4-tetrahydrocyclopent[b]-indole-(suffix listed below) PREFIX/SUFFIX |
|---|---|---|---|---|---|---|---|---|
| | $R^3$ | $R^4$ | $R^1$ | $R^2$ | $R^7$ | m | n | |
| 26 | H | H | $CH_3$ | H | $CH_3$ | 2 | 2 | 3-methyl//3-propionic acid, nmr (CDCl$_3$) δ 1.35 (s,3H), 3.55 (s,3H) |
| 27 | H | H | $CH_3$ | H | $C_2H_5$ | 2 | 2 | 3-methyl//3-propionic acid ethyl ester, nmr (CDCl$_3$) δ 1.15 (t, j = 7, 3H), 1.35 (s,3H), 4.1 (q, J = 7, 2H) |
| 28 | H | H | $C_2H_5$ | H | $CH_3$ | 2 | 2 | 3-ethyl//3-propionic acid methyl ester |
| 29 | 2-$CH_3$ | H | $C_2H_5$ | H | $CH_3$ | 2 | 1 | 3-ethyl-5-methyl//3-acetic acid methyl ester |
| 30 | 2-$C_2H_5$ | H | $C_2H_5$ | H | $CH_3$ | 2 | 1 | 3,5-diethyl//3-acetic acid methyl ester |
| 31 | 2-(n-$C_3H_7$) | H | $C_2H_5$ | H | $CH_3$ | 2 | 1 | 3-ethyl-5-propyl//3-acetic acid methyl ester |
| 32 | 4-Br | $CH_3$ | $C_2H_5$ | H | $CH_3$ | 2 | 1 | 7-bromo-3-ethyl-4-methyl//3-acetic acid methyl ester |
| 33 | H | H | n-$C_3H_7$ | H | $CH_3$ | 2 | 0 | 3-propyl//3-carboxylic acid methyl ester |
| 34 | 4-OH | H | i-$C_3H_7$ | H | $CH_3$ | 2 | 0 | 7-hydroxy-3-isopropyl//3-carboxylic acid methyl ester |
| 35 | H | H | n-$C_4H_9$ | H | $CH_3$ | 2 | 0 | 3-butyl//3-carboxylic acid methyl ester |

TABLE III

| | Hydrazine of Formula 2 | | Starting Material of Formula 3 | | | | | Product: (Prefix listed below)-5,6,7,8,9,10-hexahydrocyclohept-[b]indole - (suffix listed below) |
|---|---|---|---|---|---|---|---|---|
| Ex. | $R^3$ | $R^4$ | $R^1$ | $R^2$ | $R^7$ | m | n | PREFIX//SUFFIX |
| 36 | H | H | $CH_3$ | H | $C_2H_5$ | 4 | 0 | 6-methyl//6-carboxylic acid ethyl ester |
| 37 | 2-$CH_3$ | H | $CH_3$ | H | $C_2H_5$ | 4 | 0 | 4,6-dimethyl//6-carboxylic acid ethyl ester |
| 38 | H | H | $C_2H_5$ | H | $C_2H_5$ | 4 | 0 | 6-ethyl//6-carboxylic acid ethyl ester |
| 39 | H | H | $C_2H_5$ | 4-$CH_3$ | $C_2H_5$ | 4 | 0 | 6-ethyl-10-methyl//6-carboxylic acid ethyl ester |

EXAMPLE 40

1,2,3,4-Tetrahydro-1-methylcarbazole-1-propionic Acid Methyl Ester (5, $R^1$ and $R^7$ = $CH_3$, $R^2$, $R^3$ and $R^4$ = H, m = 3 and n = 2)

A mixture of phenylhydrazine (1.08 g), 1-methyl-2-oxocyclohexanepropionic acid methyl ester (1.98 g), described in Example 6, and ethanol is heated at reflux for 3 hr. The mixture is evaporated to dryness keeping the temperature of the mixture at about 40° C. The residue is heated with 200 ml of 10% aqueous sulfuric acid at reflux temperature for 1 hr. The mixture is cooled and extracted with ether. The extract is washed with 10% sodium hydroxide and brine, and then evaporated. The residue is subjected to chromatography on silica gel. Elution with benzene gives 1,2,3,3a,4,5-hexahydro-3a-methyl-6H-pyrido[3,2,1-jk]carbazol-6-one (6, $R^1$ = $CH_3$, $R^2$ and $R^3$ = H, m = 3 and n = 2) mp 93°-95° C. Further elution with 5% ethyl acetate in hexane as the eluant gives the title compound, nmr (CDCl$_3$) δ 1.27 (s, 3H), 3.6 (s, 3H), 7.0–7.6 (m, 4H), 7.9 (b, 1H).

In the same manner but replacing 1-methyl-2-oxocyclohexanepropionic acid methyl ester with an equivalent amount of 1-ethyl-2-oxocyclohexanepropionic acid methyl ester, described in Example 6, 3a-ethyl-1,2,3,3a,4,5-hexahydro-6H-pyrido[3,2,1-jk]carbazol-6-one, mp 97°-99° C., and 1-ethyl-1,2,3,4-tetracarbazole-1-propionic acid methyl ester, $\nu_{max}^{CHCl_3}$ 1738 cm$^{-1}$ are obtained.

EXAMPLE 41

6-Methyl-5,6,7,8,9,10-hexahydrocyclohept[b]indole-6-acetic acid methyl ester (5, $R^1$ and $R^7$ = $CH_3$, $R^2$, $R^3$ and $R^4$ = H, m = 4 and n = 1)

A mixture of the compound of formula 3, 1-methyl-2-oxocycloheptaneacetic acid methyl ester (16 g, 0.08 mole), described in Example 10, phenylhydrazine hydrochloride (12 g, 0.08 mole), phenylhydrazine (8 g, 0.07 mole) and anhydrous ethanol (100 ml) is heated at reflux for 20 hr. After cooling, water is added and the reaction mixture is extracted with benzene (2X). Evaporation to dryness of the organic layer affords a residue. The residue is heated with a 20% sulfuric acid solution (230 ml) at reflux (oil bath at 150° C.) for 1 hr. The reaction mixture is poured on ice and extracted with benzene and ether. Evaporation to dryness affords a residue which is subjected to chromatography on silica gel (500 g) using benzene as eluant. The title compound, $\nu_{max}^{CHCl_3}$ 1736 cm$^{-1}$ is eluted first, followed by 2,2a,3,4,5,6-hexahydro-2a-methyl-1H-10b-azabenzo[a]cyclopent[d]azulen-1-one (6, $R^1$ = $CH_3$, $R^2$ and $R^3$ = H, m = 4 and n = 1), nmr (CDCl$_3$) δ 1.42 (s, 3H), 2.90 (s, 2H), 7.0–7.7 (m, 3H), 7.9–8.2 (m, 1H), followed by 2,4,4a,5,6,7,8,9-octahydro-4a-methyl-2-phenyl-3H-cyclohepta[c]pyridazin-3-one (14, $R^1$ = $CH_3$, $R^2$ and $R^3$ = H and m = 4), nmr (CDCl$_3$) δ 1.18 (s, 3H), 2.18 (d, J = 16.5, 2H), 7.1–7.7 (m, 5H).

Further examples of compounds of formula 5 which can be prepared by the procedures of Examples 40 and 41 are listed in Tables IV and V. In each of the cases an equivalent amount of the appropriate hydrazine of formula 2 and the starting material of formula 3, listed therein, are used in place of starting material of formula 3, and hydrazine noted in Examples 40 and 41. Note that when $R^4$ is hydrogen, and m and n are either the integers two and two, three and two, four and one or four and two, respectively, the corresponding compound of formula 6 may be isolated as well by chromatography according to the procedures of either Example 40 or 41. Likewise when $R^4$ is hydrogen and n is the integer one, the corresponding compound 14 may be isolated.

TABLE IV

| | Hydrazine of Formula 2 | | Starting Material of Formula 3 | | | | | Product:(Prefix Listed Below)-1,2,3,4-tetrahydrocarbazole-(suffix listed below) |
|---|---|---|---|---|---|---|---|---|
| Ex. | $R^3$ | $R^4$ | $R^1$ | $R^2$ | $R^7$ | m | n | Prefix//Suffix |
| 42 | 2-$C_2H_5$ | H | $CH_3$ | H | $CH_3$ | 3 | 2 | 8-ethyl-1-methyl//1-propionic acid methyl ester, nmr (CDCl$_3$) δ 1.32 (t, J = 7, 6H), 3.6 (s, 3H), 7.2 (m, 3H), 7.9 (b, 1H) |
| 43 | 4-Cl | H | $CH_3$ | H | $CH_3$ | 3 | 2 | 6-chloro-1-methyl//1-propionic acid methyl ester, 1728 cm$^{-1}$, the corresponding compound of formula 6, 9-chloro-1,2,3,3a,-4,5-hexahydro-3a-methyl-6H-pyrido[3,2,1-jk]carbazol-6-one has $\nu_{max}^{CHCl_3}$ 1699 cm$^{-1}$ |
| 44 | 4-CF$_3$ | H | $C_2H_5$ | H | $CH_3$ | 3 | 2 | 1-ethyl-6-trifluoromethyl//1-propionic acid methyl ester |
| 45 | H | H | n-$C_3H_7$ | H | H | 3 | 2 | 1-propyl//1-propionic acid |
| 46 | 2-$C_2H_5$ | $C_2H_5$ | $CH_3$ | H | $CH_3$ | 3 | 2 | 8,9-diethyl-1-methyl//1-propionic acid methyl ester |
| 47 | 2-$CH_3$ | $CH_3$ | n-$C_3H_7$ | 4-$CH_3$ | $CH_3$ | 3 | 2 | 4,8,9-trimethyl-1-propyl//1- |

TABLE IV-continued

| | Hydrazine of Formula 2 | | Starting Material of Formula 3 | | | | | Product:(Prefix Listed Below)-1,2,3,4-tetrahydrocarbazole-(suffix listed below) |
|---|---|---|---|---|---|---|---|---|
| Ex. | $R^3$ | $R^4$ | $R^1$ | $R^2$ | $R^7$ | m | n | Prefix//Suffix |
| 48 | H | H | n-$C_4H_9$ | H | $CH_3$ | 3 | 2 | propionic acid methyl ester 1-butyl//1-propionic acid methyl ester |

TABLE V

| | Hydrazine of Formula 2 | | Starting Material of Formula 3 | | | | | Product: (Prefix Listed Below)-5,6,7,8,9,10-hexahydrocyclohept[b]indole-(suffix listed below) |
|---|---|---|---|---|---|---|---|---|
| Ex. | $R^3$ | $R^4$ | $R^1$ | $R^2$ | $R^7$ | m | n | Prefix//Suffix |
| 49 | H | H | $C_2H_5$ | H | $CH_3$ | 4 | 1 | 6-ethyl//-6-acetic acid methyl ester |
| 50 | 2-$CH_3$ | H | $CH_3$ | H | $CH_3$ | 4 | 1 | 4,6-dimethyl//-6-acetic acid methyl ester |
| 51 | 4-OCOCH$_3$ | H | $C_2H_5$ | H | $C_2H_5$ | 4 | 1 | 2-acetoxy-6-ethyl//-6-acetic acid ethyl ester |
| 52 | 4-Cl | H | n-$C_3H_7$ | H | $C_2H_5$ | 4 | 1 | 2-chloro-6-propyl//-6-acetic acid ethyl ester |
| 53 | 2-(n-$C_3H_7$) | H | n-$C_3H_7$ | H | $C_2H_5$ | 4 | 2 | 4,6-dipropyl//-6-propionic acid ethyl ester |
| 54 | 4-$CH_3$ | $CH_3$ | n-$C_3H_7$ | H | $C_2H_5$ | 4 | 2 | 2,5-dimethyl-6-propyl//-6-propionic acid ethyl ester |
| 55 | 3-$CF_3$ | $CH_3$ | $CH_3$ | 4-$CH_3$ | $CH_3$ | 4 | 2 | 5,6,10-trimethyl-3-trifluoromethyl//-6-propionic acid methyl ester |

EXAMPLE 56

1,2,3,4-Tetrahydro-1-methylcarbazole-1-acetic Acid (5, $R^1 = CH_3$, $R^2$, $R^3$, $R^4$, and $R^7 = H$, m = 3 and n = 1)

A mixture of the compound of formula 5 having $R^7$ = lower alkyl, 1,2,3,4-tetrahydro-1-methylcarbazole-1-acetic acid methyl ester (5.6 g, 21.8 mmole), described in Example 11, anhydrous potassium carbonate (1.52 g, 11.0 mmole), methanol (65 ml) and water (6.5 ml) is stirred and heated at reflux under nitrogen for 20 hr. Evaporation to dryness of the mixture affords the potassium salt of the title compound. The salt is taken up in water and the solution extracted with ether. The aqueous phase is then rendered acidic with 6N HCl and extracted with ether. This latter extract is washed with brine, dried (MgSO$_4$) and concentrated. The residue crystallizes on trituration with a benzene-hexane (4:1) mixture to afford the title compound, mp 188°–189° C., $\nu_{max}^{CHCl_3}$ 3410, 1719 cm$^{-1}$.

By following the procedure of Example 56 but using an equivalent amount of the appropriate tricyclic compound of formula 5 having $R^7$ = lower alkyl, for example those described in Examples 11–55 instead of 1,2,3,4-tetrahydro-1-methylcarbazole-1-acetic acid methyl ester, then the corresponding acids of formula 5 are obtained. For example by following the procedure of Example 56 but replacing 1,2,3,4-tetrahydro-1-methylcarbazole-1-acetic acid methyl ester with an equivalent amount of 1-ethyl-1,2,3,4-tetrahydrocarbazole-1-acetic acid methyl ester, described in Example 11, the 1-ethyl analog of the title compound, 1-ethyl-1,2,3,4-tetrahydrocarbazole-1-acetic acid, mp 148°–150° C. after recrystallization from benzene, is obtained.

Examples of other such compounds of formula 5 in which $R^7$ is hydrogen are listed in Tables VI, VII and VIII together with the requisite starting material. In each case the starting material is noted by the example in which it is prepared.

TABLE VI

| Example | No. of the Example in which the Starting Material of Formula 5 is Prepared | Product: (Prefix Listed Below)-1,2,3,4-tetrahydrocarbazole-(suffix listed below) Prefix//Suffix |
|---|---|---|
| 57 | 12 or 12a | 1-propyl//1-acetic acid, $\nu_{max}^{CHCl_3}$ 3490 - 3430, 1740, 1705 cm$^{-1}$, nmr (CDCl$_3$) δ 0.85 (t, j = 7, 3H), 2.7 – 2.75 (s, 4H), 6.9 – 7.6 (m, 4H), see also Example 12b. |
| 58 | 13 | 1,8-dimethyl//1-acetic acid |
| 59 | 14 | 5-(and 7-)ethyl-1,9-dimethyl//1-acetic acid |
| 60 | 16 | 1,8-diethyl//1-acetic acid mp 119 – 121° C |
| 61 | 17 | 1-ethyl-8-propyl//1-acetic acid. mp 127 – 128° C |
| 62 | 18 | 1-ethyl-8-isopropyl//1-acetic acid, mp 181 – 184° C, nmr (CDCl$_3$) δ 0.9 (t, J = 7, 3H), 1.35 (d, J = 7, 6H), 1.85 (m, 6H), 2.6 (m, 2H), 2.8 (s, 2H), 3.2 (m, 1H), 7.2 (m, 3H), 9.2 (s, 1H), 11.4 (s, 1H) |
| 63 | 19 | 8-chloro-1-ethyl//1-acetic acid |
| 64 | 21 | 1-ethyl-6-methoxy//1-acetic acid, mp 95 – 97° C |
| 65 | 22 | 1,3-diethyl-5-(and 7-)ethoxy//1- |

TABLE VI-continued

| Example | No. of the Example in which the Starting Material of Formula 5 is Prepared | Product: (Prefix Listed Below)-1,2,3,4-tetrahydrocarbazole-(suffix listed below) Prefix//Suffix |
|---|---|---|
| | | carboxylic acid |
| 66 | 23 | 1-methyl//1-carboxylic acid |
| 67 | 24 | 1-ethyl-6-propionoxy//1-carboxylic acid |
| 68 | 25 | 1,9-diethyl-8-trifluoromethyl//1-carboxylic acid |
| 69 | 40 (title compound) | 1-methyl//1-propionic acid, mp 204 – 206° C |
| 70 | 40 (1-ethyl-1,2,3,4-tetracarbazole-1-propionic acid methyl ester) | 1-ethyl//1-propionic acid, mp 141 – 142° C |
| 71 | 42 | 8-ethyl-1-methyl//1-propionic acid, mp 134 – 136° C |
| 72 | 43 | 6-chloro-1-methyl//1-propionic acid, mp 142 – 144° C |
| 73 | 44 | 1-ethyl-6-trifluoromethyl//1-propionic acid |
| 74 | 45 | 1-propyl//1-propionic acid |
| 75 | 46 | 8,9-diethyl-1-methyl//-propionic acid, nmr (CDCl$_3$) δ 1.15 (t, J = 8, 3H), 1.30 (t, J = 7, 3H), 1.45 (s, 3H), 3.0 (q, J = 8, 2H), 4.35 (q, J = 7, 2H), 6.9 – 7.4 (m, 3H) |
| 76 | 47 | 4,8,9-trimethyl-1-propyl//1-propionic acid |
| 77 | 48 | 1-butyl//1-propionic acid |

TABLE VII

| Example | No. of the Example in which the Starting Material of Formula 5 is Prepared | Product: (Prefix Listed Below)-1,2,3,4-tetrahydrocyclopent[b]-indole-(suffix listed below) Prefix//Suffix |
|---|---|---|
| 78 | 26 or 27 | 3-methyl//3-propionic acid, mp 182 – 184° C |
| 79 | 28 | 3-ethyl//3-propionic acid |
| 80 | 29 | 3-ethyl-5-methyl//3-acetic acid |
| 81 | 30 | 3,5-diethyl//3-acetic acid |
| 82 | 31 | 3-ethyl-5-propyl//3-acetic acid |
| 83 | 32 | 7-bromo-3-ethyl-4-methyl//3-acetic acid |
| 84 | 33 | 3-propyl//3-carboxylic acid |
| 85 | 34 | 7-hydroxy-3-isopropyl//3-carboxylic acid |
| 86 | 35 | 3-butyl//3-carboxylic acid |

TABLE VIII

| Example | No. of the Example in which the Starting Material of Formula 5 is Prepared | Product: (Prefix Listed Below)-5,6,7,8,9,10-hexahydrocyclohept-[b]indole-(suffix listed below) Prefix//Suffix |
|---|---|---|
| 87 | 41 | 6-methyl//6-acetic acid, mp 119 – 122° C |
| 88 | 36 | 6-methyl//6-carboxylic acid |
| 89 | 37 | 4,6-dimethyl//6-carboxylic acid |
| 90 | 38 | 6-ethyl//6-carboxylic acid |
| 91 | 39 | 6-ethyl-10-methyl//6-carboxylic acid |
| 92 | 49 | 6-ethyl//6-acetic acid |
| 93 | 50 | 4,6-dimethyl//6-acetic acid |
| 94 | 51 | 2-acetoxy-6-ethyl//6-acetic acid |
| 95 | 52 | 2-chloro-6-propyl//6-acetic acid |
| 96 | 53 | 4,6-dipropyl//6-propionic acid |
| 97 | 54 | 2,5-dimethyl-6-propyl//6-propionic acid |
| 98 | 55 | 5,6,10-trimethyl-3-trifluoromethyl//-6-propionic acid |

EXAMPLE 99

1-Methyl-1,2,3,4-tetrahydrocarbazole-1-propionic Acid (5; $R^1$ = CH$_3$, $R^2$, $R^3$, $R^4$ and $R^7$ = H, m = 3 and n = 2)

A solution of 1,2,3,3a,4,5-hexahydro-3a-methyl-6H-pyrido[3,2,1-jk]carbazol-6-one (0.5 g), described in Example 40, in ethanol (10 ml) and 10% sodium hydroxide solution (10 ml) is heated at reflux for 3 hr. The mixture is concentrated, diluted with water and washed with ether. The aqueous phase is rendered acidic with conc. HCl and extracted with chloroform. Concentration of the chloroform extract yields the title compound as a solid, mp 204°–206° C., identical to the product of Example 69.

In the same manner, 3a-ethyl-1,2,3,3a,4,5-hexahydro-6H-pyrido[3,2,1-jk]carbazol-6-one is converted to 1-ethyl-1,2,3,4-tetrahydrocarbazole-1-propionic acid, mp 141°–142° C., identical to the compound described in Example 70.

In the same manner 2,2a,3,4,5,6-hexahydro-2a-methyl-1H-10b-azabenzo[a]cyclopent[d]azulen-1-one, described in Example 41, is converted to 6-methyl-5,6,7,8,9,10-hexahydrocyclohept[b]indole-6-acetic acid, mp 119°–122° C., identical to the compound of the same name described in Example 87.

EXAMPLE 100

1-Ethyl-1,2,3,4-tetrahydro-9-methylcarbazole-1-acetic Acid (5; $R^1 = C_2H_5$, $R^2$, $R^3$ and $R^7 = H$, $R^4 = CH_3$, m = 3 and n = 1)

A solution of the compound of formula 5, 1-ethyl 1,2,3,4-tetrahydrocarbazole-1-acetic acid (2.0 g, 7.4 mmole), described in Example 56, in dry tetrahydrofuran (THF, 50 ml) is added dropwise under nitrogen to a stirred suspension of sodium hydride (1 g, 50% dispersion, 0.02 mole) in dry-THF (25 ml). The reaction mixture is stirred for 15 minutes after the end of the addition. The lower alkyl halide, methyliodide (1.5 ml), is added dropwise. The reaction mixture is heated initially to 40° C. then stirred for one hour at room temperature. A small amount of water is added cautiously to destroy excess sodium hydride followed by the addition of more water (50 ml). The mixture is washed with ether then rendered acidic and extracted with ether. The ether extract is dried (MgSO$_4$), treated with charcoal and filtered through diatomaceous earth. Evaporation of the ether gives an oil which on recrystallization from benzene affords the title compound, mp 140°–143° C., nmr (CDCl$_3$) δ 0.72 (t, J = 7, 3H), 1.9 (m, 6H), 2.75 (m, 4H), 3.76 (s, 3H), 7.2 (m, 4H).

By following the procedure of Example 100 and using the appropriate compound of formula 5 in which $R^4$ and $R^7$ are hydrogen, for instance those described in Examples 56–99, together with the appropriate lower alkyl halide, other compounds of formula 5 in which $R^4$ is lower alkyl are obtained. For example, the use of the compound of formula 5, 1,2,3,4-tetrahydro-1-methyl-carbazole-1-acetic acid, described in Example 56, with the lower alkyl halide, ethyl bromide, gives 9-ethyl-1-methyl-1,2,3,4-tetrahydrocarbazole-1-acetic acid, identical to the product of Example 15.

By following the procedure of Example 100 but replacing the compound of formula 5 therein with an equivalent amount of a compound of formula 5 in which $R^4$ is hydrogen and $R^7$ is lower alkyl and using the appropriate lower alkyl halide, the corresponding compounds of formula 5 in which $R^4$ is lower alkyl and $R^7$ is lower alkyl are obtained. More specifically exemplified, by replacing 1-ethyl-1,2,3,4-tetrahydrocarbazole-1-acetic acid with an equivalent amount of 1-ethyl-1,2,3,4-tetrahydrocarbazole-1-acetic acid methyl ester in the procedure of Example 100, 1-ethyl-1,2,3,4-tetrahydro-9-methyl-carbazole-1-acetic acid methyl ester, is obtained.

Additional examples are listed in Table IX, X and XI. In each case the requisite starting material of formula 5 in which $R^4$ is hydrogen is noted by the example in which it is prepared.

TABLE IX

| Example | No. of Example in Which Starting Material is Prepared | Lower Alkyl Halide | Product: (Prefix (+, Below)- 1,2,3,4-tetrahydrocarbazole- (suffix listed below) Prefix/Suffix |
|---|---|---|---|
| 101 | 57 | CH$_3$Br | 9-methyl-1-propyl//1-acetic acid |
| 102 | 58 | CH$_3$Br | 1,8,9-trimethyl//1-acetic acid |
| 103 | 60 | CH$_3$Br | 1,8-diethyl-9-methyl//1-acetic acid |
| 104 | 61 | n-C$_3$H$_7$Cl | 1-ethyl-8,9-dipropyl//1-acetic acid |
| 105 | 62 | CH$_3$Cl | 1-ethyl-8-isopropyl-9-methyl//1-acetic acid |
| 106 | 63 | C$_2$H$_{(+, l}$ | 8-chloro-1,9-diethyl//1-acetic acid |
| 107 | 64 | CH$_3$Cl | 1-ethyl-6-methoxy-9-methyl//1-acetic acid |
| 108 | 65 | C$_2$H$_5$Br | 1,3,9-triethyl-5-(and 7-)ethoxy//1-carboxylic acid |
| 109 | 66 | C$_2$H$_5$Br | 9-ethyl-1-methyl//1-carboxylic acid |
| 110 | - | C$_2$H$_5$Cl | 1,9-diethyl-6-propionoxy//1-carboxylic acid |
| 111 | 69 | CH$_3$I | 1,9-dimethyl//1-propionic acid, nmr (CDCl$_3$) δ 1.4 (s, 3H), 3.76 (s, 3H), 6.9 – 7.6 (m, 4H), 10.8 (b, 1H) |
| 112 | 69 | C$_2$H$_5$Br | 9-ethyl-1-methyl//1-propionic, acid, nmr CDCl$_3$) δ 1.4 (s, 3H), 1,35 (t, J = 7, 3H), 4.3 (q, J = 7, 2H), 7 – 7.5 (m, 4H), 11.0 (b, 1H) |
| 113 | 69 | n-C$_3$H$_7$Br | 1-methyl-9-propyl//1-propionic acid, mp 77 – 79° C |
| 114 | 70 | C$_2$H$_5$Br | 1,9-diethyl//1-propionic acid, $\theta_{max}^{CHCl_3}$ 1710 cm$^{-1}$, nmr (CDCl$_3$) δ 0.8 (t, 3H) |
| 114a | 71 | C$_2$H$_5$Br | 8,9-diethyl-1-methyl//1-propionic acid $\nu_{max}^{CHCl_3}$ 1710 cm$^{-1}$ |
| 115 | 72 | C$_2$H$_5$I | 6-chloro-9-ethyl-1-methyl//1-propionic acid $\nu_{max}^{CHCl_3}$ 3500 – 3200, 1710 cm$^{-1}$ |
| 116 | 73 | CH$_3$Br | 1-ethyl-9-methyl-6-trifluoromethyl//1-propionic acid |
| 117 | 74 | CH$_3$Br | 9-methyl-1-propyl//1-propionic acid |
| 118 | 77 | C$_2$H$_5$Br | 1-butyl-9-ethyl//1-propionic |

TABLE IX-continued

| Example | No. of Example in Which Starting Material is Prepared | Lower Alkyl Halide | Product: (Prefix (+, Below)-1,2,3,4-tetrahydrocarbazole-(suffix listed below) Prefix/Suffix |
|---|---|---|---|
| | | | acid |

TABLE X

| Example | No. of Example in Which Starting Material is Prepared | Lower Alkyl Halide | Product- (Prefix Listed Below)-1,2,3,4-tetrahydrocyclopent[b]-Indole-(suffix listed below) Prefix/Suffix |
|---|---|---|---|
| 119 | 78 | $C_2H_5I$ | 4-ethyl-3-methyl//3-propionic acid, $v_{max}^{CHCl_3}$ 2900, 1715 cm$^{-1}$ |
| 120 | 79 | $C_2H_5Br$ | 3,4-diethyl//3-propionic acid |
| 121 | 80 | $CH_3I$ | 3-ethyl-4,5-dimethyl//3-acetic acid |
| 122 | 81 | $C_2H_5Br$ | 3,4,5-triethyl//3-acetic acid |
| 123 | 82 | $CH_3Br$ | 3-ethyl-4-methyl-5-propyl//3-acetic acid |
| 124 | 83 | $C_2H_5Br$ | 7-bromo-3,4-diethyl-4-methyl//3-acetic acid |
| 125 | 84 | n-$C_3H_7I$ | 3,4-dipropyl//3-carboxylic acid |
| 126 | 85 | $CH_3Br$ | 7-hydroxy-3-isopropyl-4-methyl//3-carboxylic acid |
| 127 | 86 | $CH_3Br$ | 3-butyl-4-methyl//3-carboxylic acid |

TABLE XI

| Example | No. of Example in Which Starting Material is Prepared | Lower Alkyl Halide | Product: (Prefix Listed Below)-5,6,7,8,9,10-hexahydrocyclohept-[b]Indole-(suffix listed below) Prefix/Suffix |
|---|---|---|---|
| 128 | 87 | $C_2H_5I$ | 5-ethyl-6-methyl//6-acetic acid, mp 141 - 144° C |
| 129 | 88 | $C_2H_5I$ | 5-ethyl-6-methyl//6-carboxylic acid |
| 130 | 89 | $CH_3I$ | 4,5,6-trimethyl//6-carboxylic acid |
| 131 | 90 | $C_2H_5I$ | 5,6-diethyl//6-carboxylic acid |
| 132 | 91 | $CH_3I$ | 6-ethyl-5,10-dimethyl//6-carboxylic acid |
| 133 | 92 | $C_2H_5Br$ | 5,6-diethyl//6-acetic acid |
| 134 | 93 | $CH_3I$ | 4,5,6-trimethyl//6-acetic acid |
| 135 | 94 | $CH_3I$ | 2-acetoxy-6-ethyl-5-methyl//6-acetic acid |
| 136 | 95 | $C_2H_5Br$ | 2-chloro-5-ethyl-6-propyl//6-acetic acid |
| 137 | 96 | n-$C_3H_7$ | 4,5,6-tripropyl//6-propionic acid |

EXAMPLE 138

5-Ethyl-5,6,7,8,9,10-hexahydro-N,N,6-trimethylcyclohept[b]indole-6-ethanamine (1, $R^1$, $R^5$ and $R^6$ = $CH_3$, $R^2$ and $R^3$ = H, $R^4$ = $C_2H_5$, m = 4 and n = 1)

To a solution of the acid compound of formula 5, 5-ethyl-6-methyl-5,6,7,8,9,10-hexahydrocyclohept[b]indole-6-acetic acid (1.55 g), described in Example 128 in dry THF (60 ml) mechanically stirred at −15° C., is added triethylamine (3 ml), followed after 5 minutes by dropwise addition of ethyl chloroformate (1.5 g, 1.3 ml) at −15° C. Stirring is continued at this temperature for 30 minutes. The preceding mixture is added dropwise to a solution of an amine consisting of a cooled 40% aqueous solution of dimethylamine (100 ml). The resultant mixture is stirred for 30 minutes at room temperature. Extraction with ether (2X) affords the corresponding N,N-dimethylamide derivative, which is passed through a column of silica gel in benzene-ethyl acetate (9:1) to afford purified 5-ethyl-5,6,7,8,9,10-hexahydro-N,N,6-trimethylcyclohept[b]indole-6-acetamide (15, $R^1$, $R^5$ and $R^6$ = $CH_3$, $R^2$ and $R^3$ = H, $R^4$ = $C_2H_5$, m = 4 and n = 1), nmr (CDCl$_3$) δ 1.4 (t, J = 7, 3H), 1.73 (s, 3H), 2.8 (s,6H), 4.4 (q, J = 7, 2H), 7.3 (m, 4H).

The latter amide derivative (1.25 g) is dissolved in dry THF (25 ml) and added dropwise to a mechanically stirred mixture of lithium aluminum hydride (0.50 g) in dry THF (50 ml) at 0° C. under nitrogen. The mixture is stirred for 2 hr at room temperature under a very slow stream of nitrogen and water-THF mixture (1:1) is added carefully to the cooled mixture to destory excess hydrate. Ether is added and the solution is washed with a saturated sodium chloride solution. The organic phase is dried (MgSO$_4$) and evaporated to dryness to afford a pale yellow oil which is dissolved in 5% methanol in chloroform and poured through a column of silica gel to afford the title compound, nmr (CDCl$_3$) δ 1.4 (t, J = 7, 3H), 1.58 (s,3H), 2.14 (s,6H), 4.4 (q,2H), 7.3 (m,4H).

The corresponding hydrochloric acid addition salt (hydrochloride) of the title compound has mp 194°–197° C.

By following the procedure of Example 138 and using the appropriate acid compound of formula 5, for example, the products of Examples 56 to 137, and the appropriate amine, such as, ammonia, a lower alkylamine or di(lower)alkylamine, other compounds of formula 1 are obtained via their corresponding amide derivatives.

Examples of such compounds of formula 1 are listed as products in Tables XII, XIII and XIV. In each case the starting material is noted by the example in which it is prepared.

TABLE XII

| Ex. | No. of Ex. in which Starting Material is Prepared | Amine | Product: (Prefix listed below)-1,2,3,4-tetrahydrocarbazole-1-(suffix listed below) Prefix/Suffix |
|---|---|---|---|
| 139 | 56(title comp.) | $(CH_3)_2NH$ | N,N,1-trimethyl//ethanamine |
| 140 | 56(1-ethyl-analog of title compound) | $(CH_3)_2NH$ | N,N-dimethyl-1-ethyl//ethanamine |
| 141 | 57 | $CH_3NH_2$ | N-methyl-1-propyl//1-ethanamine |
| 142 | 58 | $(CH_3)_2NH$ | N,N,1,8-tetramethyl//ethanamine |
| 143 | 59 | $CH_3NH_2$ | 5-(and 7-)ethyl-N,1,9-trimethyl//ethanamine |
| 144 | 60 | $(C_2H_5)_2NH$ | N,N,1,8-tetraethyl//ethanamine |
| 145 | 61 | $C_2H_5NH_2$ | N,1-diethyl-8-propyl//ethanamine |
| 146 | 62 | $C_2H_5NH_2$ | N,1-diethyl-8-isopropyl//ethanamine |
| 147 | 63 | $(CH_3)_2NH$ | 8-chloro-1-ethyl-N,N-dimethyl//ethanamine |
| 148 | 64 | $C_2H_5NH_2$ | N,1-diethyl-6-methoxy//ethanamine |
| 149 | 65 | $(C_2H_5)_2NH$ | N,N,1,3-tetraethyl-5-(and 7-)ethoxy//methanamine |
| 150 | 66 | $NH_3$ | 1-methyl//methanamine |
| 151 | 67 | $(CH_3)_2NH$ | 1-ethyl-N,N-dimethyl-6-propionoxy//methanamine |
| 152 | 68 | $C_2H_5NH_2$ | N,1,9-triethyl-8-trifluoromethyl//methanamine |
| 153 | 69 | $(CH_3)_2NH$ | N,N,1-trimethyl//propanamine |
| 154 | 70 | $(CH_3)_2NH$ | 1-ethyl-N,N-dimethyl//propanamine |
| 155 | 71 | $CH_3NH_2$ | 8-ethyl-N,1-dimethyl//1-propanamine |
| 156 | 72 | $(CH_3)_2NH$ | 6-chloro-N,N,1-trimethyl//propanamine |
| 157 | 73 | $CH_3NH_2$ | 1-ethyl-N-methyl-6-trifluoromethyl//propanamine |
| 158 | 74 | $(n-C_3H_7)_2NH$ | N,N,1-tripropyl//propanamine |
| 159 | 75 | $(CH_3)_2NH$ | 8,9-diethyl-N,N,1-trimethyl//propanamine |
| 160 | 76 | $(CH_3)_2NH$ | N,N,4,8,9-pentamethyl-1-propyl//propanamine |
| 161 | 77 | $(CH_3)_2NH$ | 1-butyl-N,N-dimethyl//propanamine |
| 162 | 100 | $(CH_3)_2NH$ | 1-ethyl-N,N,9-trimethyl//ethanamine |
| 163 | 101 | $(n-C_3H_7)_2NH$ | 9-methyl-N,N,1-tripropyl//ethanamine |
| 164 | 102 | $(CH_3)_2NH$ | N,N,1,8,9-pentamethyl//ethanamine |
| 165 | 103 | $CH_3NH_2$ | 1,8-diethyl-N,9-dimethyl//ethanamine |
| 166 | 104 | $n-C_3H_7NH_2$ | 1-ethyl-N,8,9-tripropyl//ethanamine |
| 167 | 105 | $CH_3NH_2$ | 1-ethyl-8-isopropyl-N,9-dimethyl//ethanamine |
| 168 | 106 | $(C_2H_5)_2NH$ | 8-chloro-N,N,1,9-tetraethyl//ethanamine |
| 169 | 107 | $NH_3$ | 1-ethyl-6-methoxy-9-methyl-ethanamine |
| 170 | 108 | $(CH_3)_2NH$ | 1,3,9-triethyl-5-(and 7-)ethoxy-N,N-dimethyl//methanamine |
| 171 | 109 | $(C_2H_5)_2NH$ | N,N,9-triethyl-1-methyl//methanamine |
| 172 | 110 | $NH_3$ | 1,9-diethyl-6-propionoxy/methanamine |
| 173 | 111 | $(CH_3)_2NH$ | N,N,1,9-tetramethyl//propanamine |
| 174 | 112 | $(CH_3)_2NH$ | 9-ethyl-N,N,1-trimethyl//propanamine |
| 175 | 113 | $(CH_3)_2NH_2$ | N,N,1-trimethyl-9-propyl//propanamine |
| 176 | 114 | $(CH_3)_2NH_2$ | 1,9-diethyl-N,N-dimethyl//propanamine |
| 177 | 115 | $(CH_3)_2NH_2$ | 6-chloro-9-ethyl-N,N,1-trimethyl//propanamine |
| 178 | 116 | $CH_3NH_2$ | 1-ethyl-N,9-dimethyl-6-trifluoromethyl/propanamine |
| 179 | 117 | $CH_3NH_2$ | N,9-dimethyl-1-propyl//propanamine |
| 180 | 118 | $(n-C_3H_7)_2NH$ | 1-butyl-9-ethyl-N,N-dipropyl//propanamine |

TABLE XIII

| Ex. | No. of Example in Which Starting Material is Prepared | Amine | Product: (Prefix Listed Below)-1,2,3,4-tetrahydrocyclopent[b]-Indole-3-(suffix listed below) Prefix//Suffix |
|---|---|---|---|
| 181 | 78 | $(CH_3)_2NH$ | N,N,3-trimethyl//propanamine |
| 182 | 79 | $CH_3NH_2$ | 3-ethyl-N-methyl//propanamine |
| 183 | 80 | $NH_3$ | 3-ethyl-5-methyl//ethanamine |
| 184 | 81 | $C_2H_5NH_2$ | N,3,5-triethyl//ethanamine |
| 185 | 82 | $(C_2H_5)_2NH$ | N,N,3-triethyl-5-propyl//ethanamine |
| 186 | 83 | $(CH_3)_2NH$ | 7-bromo-3-ethyl-N,N,4-trimethyl//ethanamine |
| 187 | 84 | $(CH_3)_2NH$ | N,N-dimethyl-3-propyl//methanamine |
| 188 | 85 | $NH_3$ | 7-hydroxy-3-isopropyl//methanamine |
| 189 | 86 | $CH_3NH_2$ | 3-butyl-N-methyl//methanamine |
| 190 | 119 | $CH_3NH_2$ | 4-ethyl-N,3-dimethyl//propanamine |
| 191 | 120 | $(CH_3)_2NH$ | 3,4-diethyl-N,N-dimethyl//propanamine |
| 192 | 121 | $(CH_3)_2NH$ | 3-ethyl-N,N,4,5-tetramethyl//ethanamine |
| 193 | 122 | $C_2H_5NH_2$ | N,3,4,5-tetraethyl//ethanamine |

TABLE XIII-continued

| Ex. | No. of Example in Which Starting Material is Prepared | Amine | Product: (Prefix Listed Below)-1,2,3,4-tetrahydrocyclopent[b]-Indole-3-(suffix listed below) Prefix//Suffix |
|---|---|---|---|
| 194 | 123 | $(CH_3)_2NH$ | 3-ethyl-N,N,4-trimethyl-5-propyl//ethanamine |
| 195 | 124 | $NH_3$ | 7-bromo-3,4-diethyl-4-methyl//-ethanamine |
| 196 | 125 | $CH_3NH_2$ | N-methyl-3,4-dipropyl//methanamine |
| 197 | 126 | $CH_3NH_2$ | 7-hydroxy-3-isopropyl-N,4-dimethyl-methanamine |
| 198 | 127 | $(CH_3)_2NH$ | 3-butyl-N,N,4-trimethyl//methanamine |

TABLE XIV

| Ex. | No. of Example in Which Starting Material is Prepared | Amine | Product: (Prefix Listed Below)-5,6,7,8,9,10-hexahydrocyclohept[b]-Indole-6-(suffix listed below) Prefix//Suffix |
|---|---|---|---|
| 199 | 87 | $(CH_3)_2NH$ | N,N,6-trimethyl//ethanamine |
| 200 | 88 | $CH_3NH_2$ | N,6-dimethyl//methanamine |
| 201 | 89 | $CH_3NH_2$ | N,4,6-trimethyl//methanamine |
| 202 | 90 | $(C_2H_5)_2NH$ | N,N,6-triethyl//methanamine |
| 203 | 91 | $NH_3$ | 6-ethyl-10-methyl//methanamine |
| 204 | 92 | $(CH_3)_2NH$ | 6-ethyl-N,N-dimethyl//ethanamine |
| 205 | 93 | $(CH_3)_2NH$ | N,N,4,6-tetramethyl//ethanamine |
| 206 | 94 | $NH_3$ | 2-acetoxy-6-ethyl//ethanamine |
| 207 | 95 | $CH_3NH_2$ | 2-chloro-6-propyl-N-methyl//ethanamine |
| 208 | 96 | $(n-C_3H_7)_2NH$ | N,N,4,6-tetrapropyl//propanamine |
| 209 | 97 | $(CH_3)_2NH_2$ | N,N,2,5-tetramethyl-6-propyl//-propanamine |
| 210 | 98 | $NH_3$ | 5,6,10-trimethyl-3-trifluoromethyl//-propanamine |
| 211 | 128 | $(CH_3)_2NH$ | 5-ethyl-N,N,6-trimethyl//ethanamine |
| 212 | 129 | $(CH_3)_2NH$ | 5-ethyl-N,N,6-trimethy//methanamine |
| 213 | 130 | $CH_3NH_2$ | N,4,5,6-tetramethyl//methanamine |
| 214 | 131 | $(C_2H_5)_2NH$ | N,N,5,6-tetraethyl//methanamine |
| 215 | 132 | $NH_3$ | 6-ethyl-5,10-dimethyl//methanamine |
| 216 | 133 | $(CH_3)_2NH$ | 5,6-diethyl-N,N-dimethyl//ethanamine |
| 217 | 134 | $CH_3NH_2$ | N,4,5,6-tetramethyl//ethanamine |
| 218 | 135 | $(CH_3)_2NH$ | 2-acetoxy-6-ethyl-N,N,5-trimethyl//-ethanamine |
| 219 | 136 | $(CH_3)_2NH$ | 2-chloro-5-ethyl-N,N-dimethyl-6-propyl//ethanamine |
| 220 | 137 | $(n-C_3H_7)_2NH$ | N,N,4,5,6-pentapropyl//propanamine |

EXAMPLE 221

1,2,3,4-Tetrahydro-1,9-dimethylcarbazole-1-propionyl Azide (16, $R^1$ and $R^4 = CH_3$, $R^2$ and $R^3 = H$, m = 3, n = 2 and A = $CON_3$)

To a stirred, ice cold solution of 1,9-dimethyl-1,2,3,4-tetrahydrocarbazole-1-propionic acid (11.0 g, 0.04 mole), described in Example III, in dry THF (200 ml), triethylamine (10 ml, 7.25 g, 0.07 mole) and ethyl chloroformate (5.8 ml, 6.5 g, 0.06 mole) are added dropwise under nitrogen. After being stirred for 1 hr at 0° C., the resulting suspension is further cooled to −10° C. and is treated dropwise with a solution of sodium azide (3.5 g, 0.055 mole) in distilled water (18 ml). The suspension rapidly clears, leaving a gummy precipitate. After being stirred for an additional hour at −10° C., the reaction mixture is diluted with ether (100 ml). The supernatant liquid is decanted. The insoluble gummy residue is rinsed with more ether. The combined ether phases are dried ($MgSO_4$) and then evaporated under reduced pressure, without being heated, to give the title compound, nmr ($CDCl_3$) δ 1.4 (s, 3H), 3.77 (s, 3H), 7.0–7.6 (m, 4H).

EXAMPLE 222

Isocyanic Acid 2-(1,2,3,4-Tetrahydro-1,9-dimethylcarbazol-1-yl)ethyl Ester (17, $R^1$ and $R^4 = CH_3$, $R^2$ and $R^3 = H$, m = 3, n = 2 and A = NCO)

1,2,3,4-Tetrahydro-1,9-dimethylcarbazol-1-propionyl azide (11.0 g, 0.037 mole), described in Example 221, is dissolved in dry benzene (150 ml). The solution is heated at reflux for 30 minutes. Evaporation of the solvent gives the title isocyanate, $\nu_{max}^{benzene}$ 2250 cm$^{-1}$, NMR ($CDCl_3$) δ 1.4 (s, 3H), 1.0 - 2.0 (m, 6H), 2.7 (m, 2H), 3.1 (m, 2H), 3.75 (s, 3H), 6.9 - 7.6 (m, 4H).

By following serially the procedures of Examples 221 and 222, and replacing 1,9-dimethyl-1,2,3,4-tetrahydrocarbazole-1-propionic acid with other acetic and propionic acid derivatives of formula 5, as exemplified above, the corresponding isocyanates are obtained.

For example, replacement with 9-ethyl-1-methyl-1,2,3,4-tetrahydrocarbazole-1-propionic acid, described in Example 112, gives isocyanic acid 2-(9-ethyl-1,2,3,4-tetrahydro-1-methylcarbazol-1-yl)ethyl ester, nmr ($CDCl_3$) δ 1.4 (m, 6H), 4.3 (q, 2H), 7.0–7.6 (m, 4H), via 9-ethyl-1,2,3,4-tetrahydro-1-methylcarbazole-1-propionyl azide, $\nu_{max}^{CHCl_3}$ 1700 cm$^{-1}$.

Likewise, replacement with 1-methyl-9-propyl-1,2,3,4-tetrahydrocarbazole-1-propionic acid, described in Example 113, gives isocyanic acid 2-(1,2,3,4-tetrahydro-1-methyl-9-propylcarbazol-1-yl)ethyl ester, $\nu_{max}^{CHCl_3}$ 2265 cm$^{-1}$, via 1,2,3,4-tetrahydro-1-methyl-9-propylcarbazole-1-propionyl azide, $\nu_{max}^{CHCl_3}$ 2135 cm$^{-1}$.

Likewise, replacement with 8,9-diethyl-1,2,3,4-tetrahydrocarbazole-1-propionic acid, described in Example 114a, gives isocyanic acid-2-(8,9-diethyl-1,2,3,4-tetrahydro-1-methylcarbazol-1-yl)ethyl ester, $\nu_{max}^{CHCl_3}$ 2260 cm$^{-1}$, via 8,9-diethyl-1,2,3,4-tetrahydro-1-methylcarbazole-1-propionyl azide, $\nu_{max}^{CHCl_3}$ 2135 cm$^{-1}$.

Likewise, replacement with 6-chloro-9-ethyl-1-methyl-1,2,3,4-tetrahydrocarbazole-1-propionic acid, described in Example 115, gives isocyanic acid 2-(6-chloro-9-ethyl-1,2,3,4-tetrahydro-1-methylcarbazol-1-yl)ethyl ester, $\nu_{max}^{CHCl_3}$ 2250 cm$^{-1}$, via 6-chloro-9-ethyl-1,2,3,4-tetrahydro-1-methylcarbazole-1-propionyl azide, $\nu_{max}^{CHCl_3}$ 2140 cm$^{-1}$.

Likewise, replacement with 1,9-diethyl-1,2,3,4-tetrahydrocarbazole-1-propionic acid, described in Example 114, gives isocyanic acid 2-(1,9-diethyl-1,2,3,4-tetrahydrocarbazol-1-yl)ethyl ester, $\nu_{max}^{CHCl_3}$ 2260 cm$^{-1}$, via 1,9-diethyl-1,2,3,4-tetrahydrocarbazole-1-propionyl azide, $\nu_{max}^{CHCl_3}$ 2135 cm$^{-1}$.

Likewise, replacement with 4-ethyl-3-methyl-1,2,3,4-tetrahydrocyclopent[b]indole-3-propionic acide, described in Example 119, gives isocyanic acid 2-(4-ethyl-1,2,3,4-tetrahydro-3-methylcyclopent[b]indol-3-yl)ethyl ester, $\nu_{max}^{CHCl_3}$ 2255 cm$^{-1}$, via 4-ethyl-1,2,3,4-tetrahydro-3-methylcyclopent[b]indole-3-propionyl azide, $\nu_{max}^{film}$ 2125 cm$^{-1}$.

EXAMPLE 223

N-[2-(1,2,3,4-Tetrahydro-1,9-dimethylcarbazol-1-yl)ethyl]formamide (18, $R^1$ and $R^4$ = $CH_3$, $R^2$ and $R^3$ = H, m = 3, n = 2 and A = NHCHO)

Formic acid (88%, 5 ml) is added dropwise to a stirred solution of the isocyanate, isocyanic acid 2-(1,2,3,4-tetrahydro-1,9-dimethylcarbazol-1-yl)ethyl ester (10.5 g, 0.37 mole), described in Example 222, in 100 ml of dry toluene at −50° C. After the addition the mixture is allowed to rise to 20° C. and then stirred for 1 hr at that temperature and then for 1 hr at 50° C. The mixture is washed with 2N HCl and brine, dried (MgSO$_4$) and concentrated to yield the title compound. The compound may be purified by chromatography on silica gel using 10% acetone in benzene as eluant. The title compound has nmr (CDCl$_3$) δ 1.4 (s, 3H), 3.8 (s, 3H), 5.66 (b, 1H), 7.0–7.6 (m, 4H), 7.97 (s, 1H).

EXAMPLE 224

N-[2-(6-Chloro-9-ethyl-1,2,3,4-tetrahydro-1-methylcarbazol-1-yl)ethyl]formamide (18, $R^1$ = $CH_3$, $R^2$ = H, $R^3$ = 6-Cl, $R^4$ = $C_2H_5$, m = 3, n = 2 and A = NHCHO)

To a stirred suspension of sodium borohydride (3.5 g, 0.077 mole) in 20 ml of dimethoxyethane under nitrogen, a solution of isocyanic acid 2-(6-chloro-9-ethyl-1,2,3,4-tetrahydro-1-methylcarbazol-1-yl)-ethyl ester (7.0 g, 0.022 mole), described in Example 222, in 30 ml dimethoxyethane is added dropwise. The suspension is stirred for 20 hr at 25° C. The mixture is then cooled to 5° to 10° C. and water is added dropwise. The mixture is saturated with sodium chloride and extracted with ether. The organic layer is washed with water, dried (MgSO$_4$) and evaporated to afford a yellow oil. The oil is subjected to chromatography on silica gel. Subsequent elution with 5% methanol in benzene gives the title compound, $\nu_{max}^{CHCl_3}$ 3450, 1670 cm$^{-1}$.

By following the procedures of Example 223 or 224 and replacing the isocyanate therein with one of the other isocyanates of this invention, exemplified in Example 222, the corresponding formamide is obtained.

For example, replacement with isocyanic acid 2-(9-ethyl-1,2,3,4-tetrahydro-1-methylcarbazol-1-yl)ethyl ester gives N-[2-(1,2,3,4-tetrahydro-9-ethyl-1-methylcarbazol-1-yl)ethyl]formamide, $\nu_{max}^{CHCl_3}$ 3460, 1640 cm$^{-1}$.

Likewise, replacement with isocyanic acid 2-(1,2,3,4-tetrahydro-1-methyl-9-propylcarbazol-1-yl)ethyl ester gives N-[2-(1,2,3,4-tetrahydro-1-methyl-9-propylcarbazol-1-yl)ethyl]formamide, $\nu_{max}^{CHCl_3}$ 3440–3300, 1685 cm$^{-1}$.

Likewise, replacement with isocyanic acid 2-(8,9-diethyl-1,2,3,4-tetrahydro-1-methylcarbazol-1-yl)ethyl ester gives N-[2-(8,9-diethyl-1,2,3,4-tetrahydro-1-methylcarbazol-1-yl)ethyl]formamide, nmr (CDCl$_3$) δ 1.48 (s, 3H), 1.16 and 1.25 (t, J = 7, 6H), 4.36 (q, J = 7, 2H), 7.2 (m, 3H), 8.0 (m, 1H), 5.55 (b, 1H).

Likewise, replacement with isocyanic acid 2-(1,9-diethyl-1,2,3,4-tetrahydrocarbazol-1-yl)ethyl ester gives N-[2-(1,9-diethyl-1,2,3,4-tetrahydrocarbazol-1-yl)ethyl]formamide, $\nu_{max}^{CHCl_3}$ 3440 – 3400, 1695cm$^{-1}$.

Likewise, replacement with isocyanic acid 2-(4-ethyl-1,2,3,4-tetrahydro-3-methylcyclopent[b]indol-3-yl)ethyl ester gives N-[2-(4-ethyl-1,2,3,4-tetrahydro-3-methylcyclopent[b]indole-3-yl)ethyl]formamide, $\nu_{max}^{CHCl_3}$ 3440 – 3400, 1680 cm$^{-1}$.

EXAMPLE 225

N-[2-(1,2,3,4-Tetrahydro-1,9-dimethylcarbazol-1-yl)ethyl]-N-methylformamide (18, $R^1$ and $R^4$ = $CH_3$, $R^2$ and $R^3$ = H, m = 3, n = 2 and A = N(CH$_3$)CHO To a suspension of sodium hydride (2.5 g, 50% oil dispersion) in dry xylene (25 ml), is added N-[2-(1,2,3,4-tetrahydro-1,9-dimethylcarbazol-1-yl)ethyl]formamide (5.0 g, 0.018 mole), described in Example 223, in dry xylene (75 ml). The mixture is stirred and heated at reflux for 18 hr under nitrogen. Methyl iodide (10 ml) is added and the mixture heated at reflux for 5 more hr., using a dry-ice acetone condenser. After cooling, water is added to destroy excess sodium hydride and the organic layer is washed with a saturated sodium chloride solution. After drying and evaporation of the solvent, the residue is subjected to chromatography on silica gel using acetone-benzene (30%) as eluant. Concentration of the eluate gives the title compound nmr (CDCl$_3$) δ 1.4 (s, 3H), 2.8 (s, 3H), 3.76 and 3.85 (s, 3H), 7.0–7.6 (m, 4H), 7.9 (d, J = 4, 1H).

By following the procedure of Example 225 and replacing N-[2-(1,2,3,4-tetrahydro-1,9-dimethylcarbazol-1-yl)formamide with other formamide derivatives of this invention for example, those formamides described in Example 224, the corresponding N-methyl formamides are obtained.

For example, replacement with N-[2-(6-chloro-9-ethyl-1,2,3,4-tetrahydro-1-methylcarbazol-1-yl)ethyl]-formamide, described in Example 224, gives N-[2-(6-chloro-9-ethyl-1,2,3,4-tetrahydro-1-methylcarbazol-1-yl)ethyl]-N-methylformamide, $\nu_{max}^{CHCl_3}$ 1670 cm$^{-1}$.

Likewise, replacement with N-[2-(9-ethyl-1,2,3,4-tetrahydro-1-methylcarbazol-1-yl)ethyl]formamide gives N-[2-(9-ethyl-1,2,3,4-tetrahydro-1-methylcarbazol-1-yl)ethyl]-N-methylformamide, $\nu_{max}^{CHCl_3}$ 1670 cm$^{-1}$.

Likewise, replacement with N-[2-(1,2,3,4-tetrahydro-1-methyl-9-propylcarbazol-1-yl)ethyl]formamide, N-[2-(1,2,3,4-tetrahydro-1-methyl-9-propylcarbazol-1-yl)ethyl]-N-methylformamide, $\nu_{max}^{CHCl_3}$ 1670 cm$^{-1}$.

Likewise, replacement with N-[2-(8,9-diethyl-1,2,3,4-tetrahydro-1-methylcarbazol-1-yl)ethyl]formamide give N-[2-(8,9-diethyl-1,2,3,4-tetrahydro-1-methylcarbazol-1-yl)ethyl]-N-methylformamide, nmr (CDCl$_3$) δ 1.15 (2t, J = 8 and 1.5, 3H), 1.30 (t, J = 7, 3H), 1.50 (s, 3H), 2.80 (s, 3H), 4.35 (m, 2H), 7.90 (d, 1H).

Likewise, replacement with N-[2-(1,2,3,4-tetrahydro-1,9-diethylcarbazol-1-yl)ethyl]formamide gives N-[2-(1,2,3,4-tetrahydro-1,9-diethylcarbazol-1-yl)ethyl]-N-methylformamide, $\nu_{max}^{CHCl_3}$ 1670 cm$^{-1}$.

Likewise replacement with N-[2-(4-ethyl-1,2,3,4-tetrahydro-3-methylcyclopent[b]indol-3-yl)ethyl]formamide gives N-[2-(4-ethyl-1,2,3,4-tetrahydro-3-methylcyclopent[b]indol-3-yl)ethyl]-N-methylformamide, $\nu_{max}^{CHCl_3}$ 1670 cm$^{-1}$.

EXAMPLE 226

N,N,1,9-Tetramethyl-1,2,3,4-tetrahydrocarbazole-1-ethanamine (1; $R^1$, $R^4$ $R^5$ and $R^6$ = CH$_3$, $R^2$ and $R^3$ = H, m = 3, n = 1)

A solution of N-[2-(1,2,3,4-tetrahydro-1,9-dimethylcarbazol-1-yl)ethyl]-N-methylformamide (5.0 g, 0.017 mole), described in Example 225, in anhydrous THF (100 ml) is added dropwise to a stirred suspension of lithium aluminium hydride (0.50 g, 0.015 mole) in anhydrous THF (50 ml) under nitrogen. Stirring is continued for 2 hr at 25° C. The excess hydride is destroyed by dropwise addition of water to the cooled mixture. Saturated sodium chloride solution is added and the compound is extracted with ether. The ether solution is dried (MgSO$_4$) and concentraed to yield the title compound, nmr (CDCl$_3$) δ 1.4 (s, 3H), 2.19 (s, 6H), 3.8 (s, 3H), 7.0–7.6 (m, 4H).

The corresponding hydrochloric acid addition salt (hydrochloride) has mp 226°–227° C. after recrystallization from dichloromethane ether.

By following the procedure of Example 226 and replacing N-[2-(1,2,3,4-tetrahydro-1,9-dimethylcarbazol-1-yl)ethyl]-N-methylformamide with other N-methyl derivatives of this invention, for example, those N-methyl formamides described in Example 225, the corresponding tricyclic alkyl (tertiary)amines of formula 1 in which $R^5$ and $R^6$ each are methyl and n is 0 or 1 are obtained.

For example, replacement with N-[2-(6-chloro-9-ethyl-1,2,3,4-tetrahydro-1-methylcarbazol-1-yl)ethyl]-N-methylformamide gives 6-chloro-9-ethyl-N,N,1-trimethyl-1,2,3,4-tetrahydrocarbazole-1-ethanamine, nmr (CDCl$_3$) δ 1.4 (t, J = 7, 6H), 2.16 (s, 6H), 4.3 (q, J = 7, 2H), 7.3 (m, 3H), the corresponding hydrochloric acid addition salt has mp 210°–213° C.

Likewise, replacement with N-[2-(9-ethyl-1,2,3,4-tetrahydro-1-methylcarbazol-1-yl)ethyl]-N-methylformamide gives 9-ethyl-N,N,1-trimethyl-1,2,3,4-tetrahydrocarbazole-1-ethanamine, nmr (CDCl$_3$) δ 1.4 (t, J = 7, 3H), 1.5 (s, 3H), 4.4 (q, J = 7, 2H), 7.0–7.6 (m, 4H); the corresponding hydrochloric acid addition salt has mp 206°–209° C.

Likewise, replacement with N-[2-(1,2,3,4-tetrahydro-1-methyl-9-propylcarbazol-1-yl)ethyl]-N-methylformamide gives 1,2,3,4-tetrahydro-N,N,1-trimethyl-9-propylcarbazole-1-ethanamine, nmr (CDCl$_3$) δ 1.0 (t, J - 7, 3H), 1.4 (s, 3H), 2.2 (s, 6H), 4.15 (m, 2H), 7.2 (m, 4H); the corresponding hydrochloric acid addition salt has mp 230°–233° C.

Likewise, replacement with N-[2-(8,9-diethyl-1,2,3,4-tetrahydro-1-methylcarbazol-1-yl)ethyl]-N-methylformamide gives 8,9-diethyl-1,2,3,4-tetrahydro-N,N,1-trimethylcarbazole-1-ethanamine, nmr (CDCl$_3$) δ 1.18 (t, J = 7, 3H), 1.3 (t, 3H), 1.47 (s, 3H), 2.18 (s, 6H), 4.38 (q, J = 7, 2H), 6.95–7.4 (m, 3H); the corresponding maleic acid addition salt (maleate) has mp 80°–90° C.

Likewise, replacement with N-[2-(1,2,3,4-tetrahydro-1,9-diethylcarbazol-1-yl)ethyl]-N-methylformamide gives 1,9-diethyl-1,2,3,4-tetrahydro-N,N-dimethylcarbazole-1-ethanamine, nmr (CDCl$_3$) δ 0.88 (t, J = 7, 3H), 2.7 (m, 6H), 4.35 (q, J = 7, 2H), 7.2 (m, 4H); the corresponding hydrobromic acid addition salt (hydrobromide) has mp 207°–210° C.

Likewise, replacement with N-[2-(4-ethyl-1,2,3,4-tetrahydro-3-methylcyclopent[b]indol-3-yl)ethyl]formamide gives 4-ethyl-1,2,3,4-tetrahydro-3-methylcyclopent[b]indole-3-ethanamine, nmr (CDCl$_3$) δ 1.4 (t, J = 7, 3H), 1.54 (s, 3H), 4.25 (q, J - 7, 2H), 7.3 (m, 4H); the corresponding hydrobromic acid addition salt has mp 217°–220° C. (dec).

EXAMPLE 227

1,9-Diethyl-1,2,3,4-tetrahydrocarbazole-1-ethanamine (1; $R^1$ and $R^4$ = C$_2$H$_5$, $R^2$, $R^3$, $R^5$ and $R^6$ = H, m = 3, n = 1)

A suspension of the isocyanate, isocyanic acid 2-(1,9-diethyl-1,2,3,4-tetrahydrocarbazol-1-yl)ethyl ester (296 mg) described in Example 222, in 20% aqueous HCl (10 ml) is stirred and heated at 100° C. for 16 hr under nitrogen. The cooled solution is rendered alkaline witn 40% NaOH, saturated with NaCl and extracted with chloroform. The extract is dried (MgSO$_4$) and concentrated to give the title compound, nmr (CDCl$_3$) δ 0.7 (t, J = 7, 3H), 1.27 (t, J = 7, 3H), 4.0 (q, J = 7, 2H), 5.45 (b, 2H), 6.85–7.65 (m, 4H).

By following the procedure of Example 227 and replacing the isocyanate therein with other isocyanates of this invention, for example, the isocyanates exemplified in Example 222, other compounds of formula 1 in which $R^5$ and $R^6$ are hydrogen and n is 0 or 1 are obtained.

For example, replacement with isocyanic acid 2-(1,2,3,4-tetrahydro-1,9-dimethylcarbazol-1-yl)ethyl ester, described in Example 222, gives 1,2,3,4-tetrahydro-1,9-dimethylcarbazole-1-ethanamine.

Likewise, replacement with isocyanic acid 2-(9-ethyl-1,2,3,4-tetrahydro-1-methylcarbazol-1-yl)ethyl ester, described in Example 222, gives 9-ethyl-1,2,3,4-tetrahydro-1-methylcarbazole-1-ethanamine.

EXAMPLE 228

9-Ethyl-1,2,3,4-tetrahydro-N,1-dimethylcarbazole-1-ethanamine (1; $R^1$ and $R^6$ = CH$_3$, $R^2$, $R^3$ and $R^5$ = H, $R^4$ = C$_2$H$_5$, m = 3 and n = 1)

N-[2-(9-ethyl-1,2,3,4-tetrahydro-1-methylcarbazol-1-yl)ethyl]-N-methylformamide (2.1 g), described in Example 225, is heated at reflux in a solution of 10% KOH (50 ml) for 48 hr. After cooling the solution is rendered acidic and extracted with ether. The aqueous phase is then rendered alkaline and extracted with ether. The latter extract is dried (MgSO$_4$) and conc. to yield the title compound, nmr (CDCl$_3$) δ 1.4 (m, 6H), 2.37 (s, 3H), 4.3 (q, J = 7, 2H), 7.25 (m, 4H); the corresponding hydrochloric acid addition salt has mp 213°–216° C.

By following the procedure of Example 228 and replacing N-[2-(9-ethyl-1,2,3,4-tetrahydro-1-methylcarbazol-1-yl)ethyl]-N-methylformamide with other N-methyl derivatives of this invention, for example, those N-methyl formamides described in Example 225, the corresponding tricyclic alkyl (secondary) amines of formula 1 in which $R^5$ is hydrogen and $R^6$ is methyl and n is 0 or 1 are obtained.

For example, replacement with N-[2-(6-chloro-9-ethyl-1,2,3,4-tetrahydro-1-methylcarbazol-1-yl)ethyl]-

N-methylformamide gives 6-chloro-9-ethyl-1,2,3,4-tetrahydro-N,1-dimethylcarbazole-1-ethanamine.

Likewise, replacement with N-[2-(1,2,3,4-tetrahydro-1-methyl-9-propylcarbazol-1-yl)ethyl]-N-methylformamide gives 1,2,3,4-tetrahydro-N,1-dimethyl-9-propylcarbazole-1-ethanamine.

We claim:

1. A compound of the formula 1

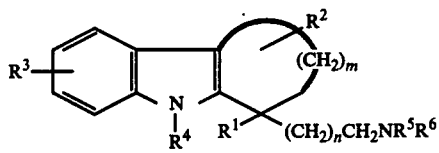

in which $R^1$ is lower alkyl, $R^2$ is hydrogen or lower alkyl, $R^3$ is hydrogen, lower alkyl, halo, hydroxy, lower alkoxy, lower alkanoyloxy or trihalomethyl, $R^4$ is hydrogen or lower alkyl, $R^5$ and $R^6$ are the same or different and are selected from the group consisting of hydrogen and lower alkyl, m is an integer from two to four and n is an integer from zero to two; or an acid addition salt with a pharmaceutically acceptable acid.

2. A compound of claim 1, wherein $R^4$ is lower alkyl.
3. A compound of claim 1, wherein m is two.
4. A compound of claim 1, wherein m is three.
5. A compound of claim 1, wherein m is four.
6. 5-Ethyl-5,6,7,8,9,10-hexahydro-N,N,6-trimethylcyclohept[b]indole-6-ethanamine, as claimed in claim 5.
7. 5-Ethyl-5,6,7,8,9,10-hexahydro-N,N,6-trimethylcyclohept[b]indole-6-ethanamine hydrochloride, as claimed in claim 5.
8. N,N,1,9-Tetramethyl-1,2,3,4-tetrahydrocarbazole-1-ethanamine, as claimed in claim 1.
9. N,N,1,9-Tetramethyl-1,2,3,4-tetrahydrocarbazole-1-ethanamine hydrochloride, as claimed in claim 1.
10. 6-Chloro-9-ethyl-N,N,1-trimethyl-1,2,3,4-tetrahydrocarbazole-1-ethanamine, as claimed in claim 1.
11. 6-Chloro-9-ethyl-N,N,1-trimethyl-1,2,3,4-tetrahydrocarbazole-1-ethanamine hydrochloride, as claimed in claim 1.
12. 9-Ethyl-N,N,1-trimethyl-1,2,3,4-tetrahydrocarbazole-1-ethanamine, as claimed in claim 1.
13. 9-Ethyl-N,N,1-trimethyl-1,2,3,4-tetrahydrocarbazole-1-ethanamine hydrochloride, as claimed in claim 1.
14. 1,2,3,4-Tetrahydro-N,N,1-trimethyl-9-propylcarbazole-1-ethanamine, as claimed in claim 1.
15. 1,2,3,4-Tetrahydro-N,N,1-trimethyl-9-propylcarbazole-1-ethanamine hydrochloride, as claimed in claim 1.
16. 1,9-Diethyl-1,2,3,4-tetrahydro-N,N-dimethylcarbazole-1-ethamine, as claimed in claim 1.
17. 1,9-Diethyl-1,2,3,4-tetrahydro-N,N-dimethylcarbazole-1-ethamine hydrobromide, as claimed in claim 1.
18. 4-Ethyl-1,2,3,4-tetrahydro-3-methylcyclopent[b]indole-3-ethamine, as claimed in claim 3.
19. 4-Ethyl-1,2,3,4-tetrahydro-3-methylcyclopent[b]indole-3-ethanamine hydrobromide, as claimed in claim 3.
20. 1,9-Diethyl-1,2,3,4-tetrahydrocarbazole-1-ethanamine, as claimed in claim 1.
21. 9-Ethyl-1,2,3,4-tetrahydro-N,1-dimethylcarbazole-1-ethanamine, as claimed in claim 1.
22. 9-Ethyl-1,2,3,4-tetrahydro-N,1-dimethylcarbazole-1-ethanamine hydrochloride, as claimed in claim 1.

* * * * *

UNITED STATES PATENT AND TRADEMARK OFFICE
CERTIFICATE OF CORRECTION

PATENT NO. : 4,128,560
DATED : December 5, 1978
INVENTOR(S) : Andre A. Asselin et al It is certified that error appears in the above-identified patent and that said Letters Patent are hereby corrected as shown below:

Column 2, lines 7-14, formula 1, "G" should read - C - at the lower portion of the right hand ring of formula 1, Column 9, line 6, "trifluorideetherate" should read - trifluoride-etherate -, Column 10, lines 10-17, formula 14, a curved line joining the two "$CH_2$" should be added to formula 14, i.e. formula 14 should read:

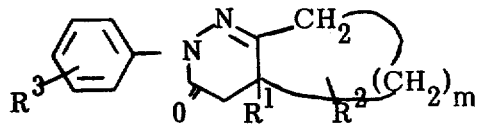

Column 14, line 38, "chromotography" should read - chromatography -,

Column 16, line 62, "chloroformhexane" should read - chloroform-hexane -,

Column 17, line 49, "1-ethyl-2-oxocyclohexanceacetic" should read -1- ethyl-2-oxocyclohexaneacetic-,

UNITED STATES PATENT AND TRADEMARK OFFICE
CERTIFICATE OF CORRECTION

PATENT NO. : 4,128,560  
DATED : December 5, 1978  
INVENTOR(S) : Andre A. Asselin et al It is certified that error appears in the above-identified patent and that said Letters Patent are hereby corrected as shown below:

Column 24, Table VI, Example 64, "1-ethyl-6-methoxy//1-acetic acid," should be aligned with the rest of the third column, Column 25, Table VI continued, Example 70, second line of second column, "tetracarbazole" should read tetrahydrocarbazole —.

Column 25, Table VI-contined, Example 73, "1-ethyl-6-trifluoromethyl//1-pro-" should be aligned with the rest to the third crown.

Column 28, Table IX, Example 110, "-$C_2H_5Cl$" in the second column should read -67 - and "1,9-diethyl-6-propionoxy // 1-" should be aligned with the rest of the fourth column, and - $C_2H_5Cl$ -inserted in the third column, Column 40, Claim 16, "ethamine" should read - ethanamine -,  
Column 40, Claim 17, "ethamine" should read - ethanamine -, and  
Column 40 Claim 18, "ethamine" should read - ethanamine -.

Signed and Sealed this

Sixteenth Day of September 1980

[SEAL]

Attest:

SIDNEY A. DIAMOND

Attesting Officer  
Commissioner of Patents and Trademarks